US010525122B2

(12) United States Patent
Kimachi et al.

(10) Patent No.: US 10,525,122 B2
(45) Date of Patent: Jan. 7, 2020

(54) VACCINE CONTAINING VIRUS-LIKE PARTICLES

(71) Applicant: KM Biologics Co., Ltd., Kumamoto-shi, Kumamoto (JP)

(72) Inventors: Kazuhiko Kimachi, Kikuchi (JP); Motoharu Abe, Kikuchi (JP); Kazuyuki Ikeda, Kikuchi (JP); Hiroto Onuma, Kikuchi (JP); Yukari Tsurudome, Kikuchi (JP); Daisuke Ikeno, Kikuchi (JP); Kiyoto Nishiyama, Kumamoto (JP); Tatsufumi Onchi, Kikuchi (JP); Yusuke Ooyama, Kumamoto (JP); Issay Asano, Kumamoto (JP); Ryoichi Kitano, Kumamoto (JP)

(73) Assignee: KM Biologics Co., Ltd., Kumamoto (JP)

( * ) Notice: Subject to any disclaimer, the term of this patent is extended or adjusted under 35 U.S.C. 154(b) by 8 days.

(21) Appl. No.: 15/326,143

(22) PCT Filed: Jul. 15, 2015

(86) PCT No.: PCT/JP2015/070297
§ 371 (c)(1),
(2) Date: Jan. 13, 2017

(87) PCT Pub. No.: WO2016/010081
PCT Pub. Date: Jan. 21, 2016

(65) Prior Publication Data
US 2017/0196965 A1 Jul. 13, 2017

(30) Foreign Application Priority Data
Jul. 18, 2014 (JP) ................................ 2014-147845

(51) Int. Cl.
*C12N 7/00* (2006.01)
*A61K 39/145* (2006.01)
*A61K 39/00* (2006.01)

(52) U.S. Cl.
CPC ............. *A61K 39/145* (2013.01); *C12N 7/00* (2013.01); *A61K 2039/5258* (2013.01);
(Continued)

(58) Field of Classification Search
None
See application file for complete search history.

(56) References Cited

U.S. PATENT DOCUMENTS 4,431,633 A * 2/1984 Machlowitz ......... A61K 39/145 424/209.1
2005/0009008 A1 1/2005 Robinson et al.
(Continued)

FOREIGN PATENT DOCUMENTS

| | | |
|---|---|---|
| CN | 1849134 | 10/2006 |
| JP | 2002-532387 | 10/2002 |

(Continued)

OTHER PUBLICATIONS

Cham et al., "Delipidation of a hepadnavirus: Viral inactivation and vaccine development,", Journal of Virological Methods, 2006, 137:160-63.
(Continued)

*Primary Examiner* — Michelle S Horning
(74) *Attorney, Agent, or Firm* — Fish & Richardson P.C.

(57) ABSTRACT

The present invention provides a vaccine containing virus-like particles derived from virus particles having an envelope, in which a lipid-component content of the virus-like particles is reduced relative to a lipid-component content of the virus particles.

15 Claims, 8 Drawing Sheets

(52) U.S. Cl.
CPC .............. *C12N 2760/16123* (2013.01); *C12N 2760/16134* (2013.01); *C12N 2760/16223* (2013.01); *C12N 2760/16234* (2013.01)

(56) References Cited

U.S. PATENT DOCUMENTS

| | | | |
|---|---|---|---|
| 2005/0032222 | A1 | 2/2005 | Cham et al. |
| 2010/0143399 | A1 | 6/2010 | Biemans et al. |

FOREIGN PATENT DOCUMENTS

| | | |
|---|---|---|
| JP | 2004-507462 | 3/2004 |
| JP | 2005-500304 | 1/2005 |
| JP | 2007-524383 | 8/2007 |
| JP | 2007-529997 | 11/2007 |
| JP | 2010-514817 | 5/2010 |
| WO | WO 00/032625 | 6/2000 |
| WO | WO 02/000266 | 1/2002 |
| WO | WO 03/000014 | 1/2003 |
| WO | 2005/016246 | 2/2005 |
| WO | 2005/020889 | 3/2005 |
| WO | 2008/081014 | 7/2008 |

OTHER PUBLICATIONS

Desombere et al., "Partial Delipidation Improves the T-Cell Antigenicity of Hepatitis B Virus Surface Antigen", Journal of Virology, 2006, 80(7):3506-14.

Groth et al., "Safety, tolerability and immunogenicity of a mammalian cell-culturederived influenza vaccine: A sequential Phase I and Phase II clinical trial.", Vaccine, 2009, 27(5):786-91.

International Search Report for PCT/JP2015/070297 dated Oct. 13, 2015, with English translation.

Kitabwalla et al., "Delipidated Retroviruses as Potential Autologous Therapeutic Vaccines—A pilot Experiment", Experimental Biology and Medicine, 2008, 233(6):732-40.

Kitabwalla et al., "Enhancement of cell mediated immune responses using lipid depleted lentivirus as immunogen: a novel approach for inducing recognition of new viral epitopes", Vaccine, 2005, 23:4666-77.

Sawai et al., "Induction of cytotoxic T-lymphocyte and antibody responses against highly pathogenic avian influenza virus infection in mice by inoculation of apathogenic H5N1 influenza virus particles inactivated with formalin", Immunology, 2008, 124:155-65.

She et al. "Surface modifications of influenza proteins upon virus inactivation by β-ropiolactone", Proteomics, 2013,13:3537-47.

Szymczakiewicz-Multanowska et al., "Safety and Immunogenicity of a Novel Influenza Subunit Vaccine Produced in Mammalian Cell Culture.", The Journal of Infectious Diseases, 2009, 200(6):841-48.

International Preliminary Report on Patentability in International Application No. PCT/JP2015/070297, dated Feb. 2, 2017, 9 pages.

Office Action in Japanese Patent Application No. P2016-534469, dated Mar. 29, 2019, 4 pages.

Office Action in Taiwanese Patent Application No. 104123240, dated Nov. 19, 2018, 8 pages.

* cited by examiner

Fig.1

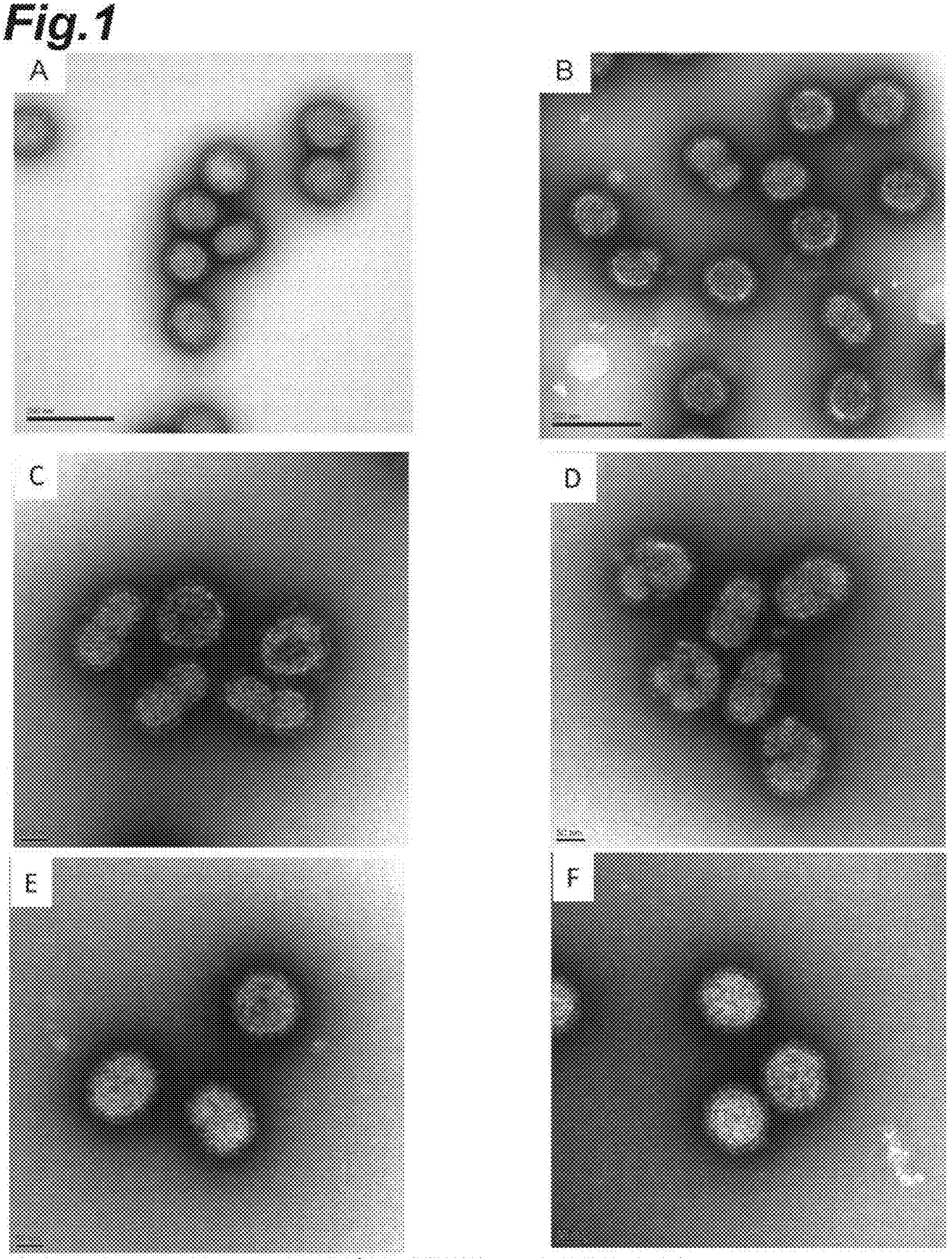

A: Sample reacted for 6 weeks at 4°C in 0.02% formalin (B/WC strain)
B: Sample reacted for 1 week at 25°C in 0.05% formalin and then treated with ether (B/WC strain)
C: Sample reacted for 1 week at 25°C in 0.08% formalin and then treated with ether (A/CA strain)
D: Sample reacted for 1 week at 25°C in 0.08% formalin and then treated with ether (A/NY strain)
E: Sample reacted for 1 week at 25°C in 0.08% formalin and then treated with ether (B/BR strain)
F: Sample reacted for 1 week at 25°C in 0.08% formalin and then treated with ether (B/MA strain)

A: Vero cell-cultured Japanese encephalitis original vaccine
B: Sample treated with ether without being subjected to glutaraldehyde fixation
C: Sample reacted for 3 days at 4°C at glutaraldehyde concentration of 0.01 w/v% and then treated with ether

VACCINE CONTAINING VIRUS-LIKE PARTICLES

TECHNICAL FIELD

The present invention relates to a vaccine containing virus-like particles. Specifically, the present invention relates to a vaccine containing virus-like particles in which a lipid-component content is reduced relative to a lipid-component content in whole particle viruses.

BACKGROUND ART

The infectious diseases caused by viruses such as an influenza virus and a Japanese encephalitis virus become severe in some cases depending on the type of virus and the infected subject. As a defense method against the infectious diseases caused by viruses, vaccination and the like are known.

CITATION LIST

Non Patent Literature

[Non-Patent Literature 1] J. Infect. Dis. 2009 200 (6) 841-848

[Non-Patent Literature 2] Vaccine 2009 27 (5) 786-791

SUMMARY OF INVENTION

Problems to be Solved by the Invention

As vaccines against viruses such as an influenza virus and a Japanese encephalitis virus, two types, an inactivated vaccine and a live vaccine, are being manufactured and marketed. Among the vaccines, the inactivated vaccine is roughly classified into a whole particle vaccine, which is prepared by treating purified virus particles with an inactivator such as formalin, and a split vaccine which is prepared by disrupting purified virus particles by using an organic solvent or a surfactant. The whole particle vaccine exhibits high immunogenicity and has an excellent infection prevention effect. However, the whole particle vaccine tends to result in strong side reactions such as a local reaction and fever. The split vaccine is a vaccine that contains viruses disrupted (split) by an organic solvent or a surfactant such that the aforementioned problem of side reactions is solved. The split vaccine is highly safe because it causes a local reaction less and hardly causes a febrile reaction. However, the split vaccine tends to exhibit low immunogenicity in children who have not yet developed basic immunity and seniors having a weakened immune response. Therefore, there is a demand for development of a vaccine which exhibits efficacy (immunogenicity) higher than that of a split vaccine and more preferably exhibits efficacy equivalent to that of a whole particle vaccine and is highly safe.

The present invention has been made in consideration of the above circumstances, and an object thereof is to provide a vaccine which exhibits high immunogenicity and is inhibited from causing side reactions.

Means for Solving the Problems

In order to achieve the aforementioned object, the inventors of the present invention conducted a thorough study. As a result, they obtained knowledge that, surprisingly, virus-like particles, in which only a lipid component of a virus envelope is reduced without disrupting (splitting) the particle structure of the virus and which have the same components and structure as the original virus except for the lipid-component content, obtained excellent scores in an immunogenicity test and a fever test. Based on the knowledge, the inventors accomplished the present invention.

That is, the present invention provides the following [1] to [15].

[1] A vaccine containing virus-like particles derived from virus particles having an envelope, in which a lipid-component content of the virus-like particles is reduced relative to a lipid-component content of the virus particles.

[2] The vaccine described in [1], in which the lipid-component content of the virus-like particles is less than 50% by mass based on the lipid-component content of the virus particles.

[3] The vaccine described in [1] or [2], in which the lipid-component content of the virus-like particles is less than 20% by mass based on the lipid-component content of the virus particles.

[4] The vaccine described in any one of [1] to [3], in which the lipid component is cholesterol.

[5] The vaccine described in any one of [1] to [4], in which the virus-like particles contain a surface antigen of the virus particles, a matrix protein or a membrane protein of the virus particles, and a nucleoprotein of the virus particles.

[6] The vaccine described in any one of [1] to [5], in which the virus-like particles contain a genomic nucleic acid derived from the virus particles.

[7] The vaccine described in any one of [1] to [6], in which the virus particles are orthomyxovirus particles, flavivirus particles, or hepatitis B virus particles.

[8] The vaccine described in [7], in which the virus particles are influenza virus particles, Japanese encephalitis virus particles, or hepatitis B virus surface antigen (HBs) particles.

[9] The vaccine described in [8], in which the virus particles are influenza virus particles.

[10] The vaccine described in [9], in which the influenza virus particles are influenza A virus particles or influenza B virus particles.

[11] The vaccine described in [9] or [10], in which the influenza virus particles are classified into an H1N1 subtype strain, an H2N2 subtype strain, an H3N2 subtype strain, an H3N8 subtype strain, an H5N1 subtype strain, an H5N2 subtype strain, an H5N6 subtype strain, an H6N1 subtype strain, an H7N3 subtype strain, an H7N7 subtype strain, an H7N9 subtype strain, an H9N2 subtype strain, or an H10N8 subtype strain.

[12] The vaccine described in any one of [8] to [11], in which the surface antigen contains hemagglutinin (HA) or neuraminidase (NA).

[13] The vaccine described in any one of [8] to [12], in which the matrix protein or the membrane protein contains an M1 protein or an M2 protein.

[14] The vaccine described in any one of [1] to [13], in which the virus-like particles have a mean particle size that is 70% to 130% of a particle size of the virus particles.

[15] The vaccine described in any one of [1] to [14], in which the virus-like particles form a peak detected at a sucrose concentration of equal to or higher than 35% when being measured by sucrose density gradient centrifugation.

The present invention also provides the following [16] to [50].

[16] A method for manufacturing a vaccine containing virus-like particles, including a step of fixing particle structures of virus particles having an envelope, and a step of performing a delipidation treatment on the fixed virus particles.

[17] The manufacturing method described in [16], in which the step of fixing includes a step of adding a fixative to a suspension A containing the virus particles.

[18] The manufacturing method described in [17], in which the fixative contains aldehydes.

[19] The manufacturing method described in [17], in which the fixative contains 1-ethyl-3-[3-dimethylaminopropyl]carbodiimide hydrochloride (EDC).

[20] The manufacturing method described in [18], in which the aldehydes are selected from the group consisting of formaldehyde, paraformaldehyde, glutaraldehyde, and a combination of these.

[21] The manufacturing method described in [20], in which the aldehydes contain formaldehyde.

[22] The manufacturing method described in [21], in which a concentration of the formaldehyde is 0.007 to 0.076 w/v % based on a total amount of the suspension A and the fixative.

[23] The manufacturing method described in [20], in which the aldehydes contain glutaraldehyde.

[24] The manufacturing method described in [23], in which a concentration of the glutaraldehyde is 0.002 to 0.05 w/v % based on a total amount of the suspension A and the fixative.

[25] The manufacturing method described in any one of [16] to [24], in which the step of performing a delipidation treatment includes a step of adding a delipidation agent to a suspension B containing the fixed virus particles.

[26] The manufacturing method described in [25], in which the delipidation agent is selected from the group consisting of diethyl ether, diisopropyl ether, methyl acetate, ethyl acetate, and a combination of these.

[27] The manufacturing method described in [26], in which the delipidation agent contains diethyl ether.

[28] The manufacturing method described in [27], in which a concentration of the diethyl ether is equal to or higher than 10 vol % based on a total amount of the suspension B and the delipidation agent.

[29] The manufacturing method described in any one of [25] to [28], in which the delipidation agent further contains a surfactant.

[30] The manufacturing method described in any one of [16] to [29], in which the virus particles are recovered after being caused to infect a culture cell or a chicken egg.

[31] The manufacturing method described in [30], in which the culture cell is a Vero cell or an MDCK cells.

[32] A method for preventing viral infectious diseases, including a step of administering a vaccine, which contains virus-like particles derived from virus particles having an envelope, to a subject, in which a lipid-component content of the virus-like particles is reduced relative to a lipid-component content of the virus particles.

[33] The method described in [32], in which the subject is a mammal.

[34] The method described in [32], in which the subject is a human being.

[35] The method described in any one of [32] to [34], in which the lipid-component content of the virus-like particles is less than 50% by mass based on the lipid-component content of the virus particles.

[36] The method described in any one of [32] to [35], in which the lipid-component content of the virus-like particles is less than 20% by mass based on the lipid-component content of the virus particles.

[37] The method described in any one of [32] to [36], in which the lipid component is cholesterol.

[38] The method described in any one of [32] to [37], in which the virus-like particles contain a surface antigen of the virus particles, a matrix protein or a membrane protein of the virus particles, and a nucleoprotein of the virus particles.

[39] The method described in any one of [32] to [38], in which the virus-like particles contain a genomic nucleic acid derived from the virus particles.

[40] The method described in any one of [32] to [39], in which the virus particles are orthomyxovirus particles, flavivirus particles, or hepatitis B virus particles.

[41] The method described in [40], in which the virus particles are influenza virus particles, Japanese encephalitis virus particles, or hepatitis B virus surface antigen (HBs) particles.

[42] The method described in [41], in which the virus particles are influenza virus particles.

[43] The method described in [42], in which the influenza virus particles are influenza A virus particles or influenza B virus particles.

[44] The method described in [42] or [43], in which the influenza virus particles are classified into an H1N1 subtype strain, an H2N2 subtype strain, an H3N2 subtype strain, an H3N8 subtype strain, an H5N1 subtype strain, an H5N2 subtype strain, an H5N6 subtype strain, an H6N1 subtype strain, an H7N3 subtype strain, an H7N7 subtype strain, an H7N9 subtype strain, an H9N2 subtype strain, or an H10N8 subtype strain.

[45] The method described in any one of [41] to [44], in which the surface antigen contains hemagglutinin (HA) or neuraminidase (NA).

[46] The method described in any one of [41] to [45], in which the matrix protein or the membrane protein contains an M1 protein or an M2 protein.

[47] The method described in any one of [32] to [46], in which the virus-like particles have a mean particle size that is 70% to 130% of a particle size of the virus particles.

[48] The method described in any one of [32] to [47], in which the virus-like particles form a peak detected at a sucrose concentration of equal to or higher than 35% when being measured by sucrose density gradient centrifugation.

[49] Use of virus-like particles derived from virus particles having an envelope in manufacturing a vaccine against viruses, in which a lipid-component content of the virus-like particles is reduced relative to a lipid-component content of the virus particles.

[50] Virus-like particles which are for use in preventing viral infectious diseases and derived from virus particles having an envelope, in which a lipid-component content of the virus-like particles is reduced relative to a lipid-component content of the virus particles.

Effects of the Invention

According to the present invention, it is possible to provide a vaccine which exhibits high immunogenicity and is inhibited from causing side reactions.

BRIEF DESCRIPTION OF DRAWINGS

FIG. 1 shows pictures of influenza virus particles and virus-like particles derived therefrom that were taken with an electron microscope (formalin treatment).

EMBODIMENTS FOR CARRYING OUT THE INVENTION

Figure 2:
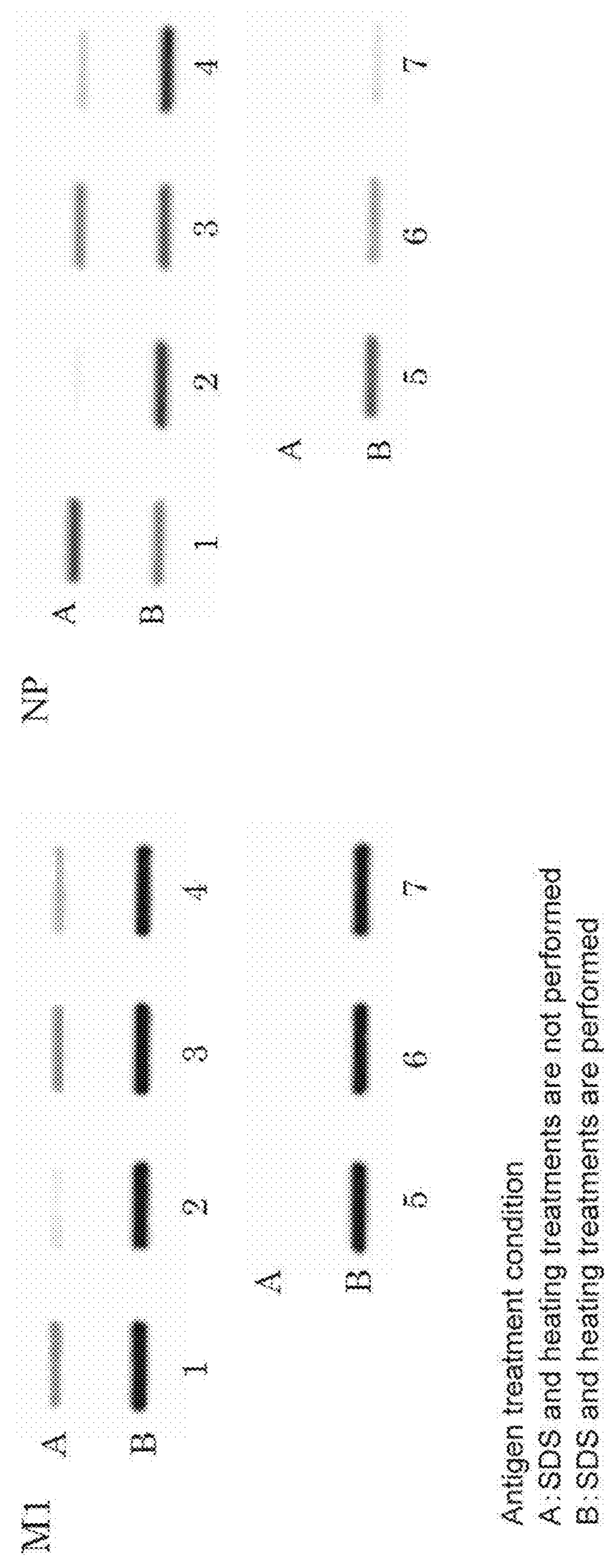
FIG. 2 shows pictures showing the results of a Slot-blot method that reveals whether or not the virus-like particles derived from the influenza virus particles contain a matrix protein (M1) and a nucleoprotein (NP).

Hereinafter, suitable embodiments of the present invention will be specifically described, but the present invention is not limited to the following embodiments.

(Vaccine Containing Virus-Like Particles)

A vaccine according to the present embodiment is a vaccine containing virus-like particles derived from virus particles having an envelope (hereinafter, referred to as "enveloped virus particles" in some cases), in which a lipid-component content of the virus-like particles is reduced relative to a lipid-component content of the virus particles. The immunogenicity of the vaccine is equal to or higher than the immunogenicity of a split vaccine and may be equal to or higher than the immunogenicity of a whole particle vaccine. The aforementioned vaccine is inhibited from causing side reactions such as a local reaction and fever, such that it causes the side reactions less than a split vaccine does or to the same extent as a split vaccine does.

The "virus-like particles derived from virus particles having envelopes" (hereinafter, simply referred to as "virus-like particles" in some cases) mean structures which are obtained by altering virus particles having envelopes and have external and internal structures similar to those of the virus particles. In the virus-like particles according to the present embodiment, the particle structures may be fixed, such that the virus-like particles maintain the same granularity as the original virus particles from which the virus-like particles are derived.

Examples of the lipid component contained in the enveloped virus particles include cholesterol, phosphatidylcholine, phosphatidylethanolamine, phosphatidylserine, sphingomyelin, and the like. The lipid component may be cholesterol.

The lipid-component content can be measured by a known method, and examples thereof include a cholesterol oxidase•DAOS method, a fluorochrome method, mass spectrometry, and the like.

For example, in a case where the lipid-component content is measured by a fluorochrome method, the lipid-component content of the aforementioned virus-like particles may be, based on a lipid-component content of the aforementioned virus particles, equal to or less than 80% by mass, equal to or less than 75% by mass, equal to or less than 70% by mass, equal to or less than 60% by mass, equal to or less than 50% by mass, less than 50% by mass, equal to or less than 40% by mass, equal to or less than 30% by mass, equal to or less than 20% by mass, or less than 20% by mass. If the lipid-component content of the virus-like particles is within the above range based on the lipid-component content of the virus particles, in a case where the virus-like particles used for vaccination, side reactions such as a febrile reaction tends to be more easily suppressed. A lower limit of the lipid-component content of the virus-like particles is not particularly limited, but may be, for example, based on the lipid-component content of the virus particles, equal to or greater than 1% by mass, equal to or greater than 5% by mass, equal to or greater than 10% by mass, or equal to or greater than 15% by mass.

Examples of the virus particles having envelopes include poxvirus particles, herpesvirus particles, orthomyxovirus particles, paramyxovirus particles, rhabdovirus particles, coronavirus particles, arenavirus particles, togavirus particles, flavivirus particles, bunyavirus particles, retrovirus particles, hepadnavirus particles, and hepatitis B virus particles. The aforementioned virus particles may be virus particles which have a fixed particle structure and contain a surface antigen and a matrix protein or a membrane protein. Examples of such virus particles include orthomyxovirus particles, paramyxovirus particles, rhabdovirus particles, and flavivirus particles. The orthomyxovirus particles may be influenza virus particles. The flavivirus particles may be Japanese encephalitis virus particles. The hepatitis B virus particles may be hepatitis B virus surface antigen (HBs) particles.

Examples of the influenza virus particles include influenza A virus particles and influenza B virus particles. Examples of the influenza A virus particles include influenza particles which are classified into an H1N1 subtype strain, an H2N2 subtype strain, an H3N2 subtype strain, an H3N8 subtype strain, an H5N1 subtype strain, an H5N2 subtype strain, an H5N6 subtype strain, an H6N1 subtype strain, an H7N3 subtype strain, an H7N7 subtype strain, an H7N9 subtype strain, an H9N2 subtype strain, or an H10N8 subtype strain.

The virus-like particles may contain a surface antigen of virus particles, a matrix protein or a membrane protein of virus particles, and a nucleoprotein of virus particles. If such a constitution is adopted, the immunogenicity tends to be further improved.

In a case where the virus particles are influenza virus particles, examples of the surface antigen include hemagglutinin (HA) and neuraminidase (NA).

In a case where the virus particles are influenza virus particles, examples of the matrix protein include an M1 protein, and examples of the membrane protein include an M2 protein.

The virus-like particles may contain a genomic nucleic acid derived from the virus particles. A content of the genomic nucleic acid of the virus-like particles may be, based on a content of the genomic nucleic acid of the virus particles (or inactivated whole particle viruses), may be equal to or greater than 50% by mass, equal to or greater than 80% by mass, equal to or greater than 85% by mass, equal to or greater than 90% by mass, equal to or greater than 95% by mass, or 100% by mass. An upper limit of the content of the genomic nucleic acid of the virus-like particles is not particularly limited, but may be, based on the content of the genomic nucleic acid of the virus particles, equal to or less than 100% by mass, equal to or less than 99% by mass, or equal to or less than 95% by mass.

The content of the genomic nucleic acid can be measured by a known method. Examples of the method include a fluorescence method, an absorbance method, a PCR method, and the like.

In the related art, a virus-like particle (VLP) preparation method is known in which a gene, which encodes a surface antigen, a matrix protein, or a membrane protein constituting virus particles, is introduced into a host (for example, a yeast cell, an insect cell, and the like), proteins thereof are expressed in the host, and then virus particles are formed. VLP obtained by such a gene recombination technique does not contain a genomic nucleic acid and a nucleoprotein derived from virus. In contrast, as will be described later, the virus-like particles according to the present embodiment are prepared by infecting a host with virus particles, allowing the viruses to grow, and then performing a fixation treatment and a delipidation treatment, which will be described later, on the obtained virus particles. Therefore, unlike VLP prepared by a gene recombination technique, the virus-like particles according to the present embodiment can contain a genomic nucleic acid and a nucleoprotein derived from the virus particles.

The genomic nucleic acid derived from the virus particles can function as an adjuvant. For example, as inactivated poliovirus vaccines, there are a D antigen containing viral genomic RNA and a C antigen not containing viral genomic RNA. The C antigen exhibits weak immunogenicity and is not effective as a vaccine antigen, and it is the D antigen that is the only molecule species effective as a vaccine antigen. This implies that the viral genomic RNA contained in a vaccine is important for the vaccine to exert effects. Therefore, from the viewpoint of further improving the immunogenicity of a vaccine, the virus-like particles according to the present embodiment may contain a genomic nucleic acid derived from the virus particles. A nucleoprotein induces the cellular immunity of a cytotoxic T cell or the like against a virus and exerts an effect in viral clearance. Consequently, the virus-like particles according to the present embodiment may contain the nucleoprotein.

The virus-like particles according to the present embodiment can induce a Th1 response, whereas a split influenza vaccine induces a Th2 response. An IgG2a subclass antibody induced in a mouse due to the Th1 response has a better defensive ability against an infection with an influenza virus compared to an IgG1 subclass antibody induced due to the Th2 response. Therefore, the aforementioned virus-like particles could further improve the efficacy. That is, the virus-like particles may induce the antigen-specific IgG2a more than the antigen-specific IgG1 in a mouse.

In a case where the virus-like particles are measured by sucrose density gradient centrifugation, high-performance liquid chromatography, and/or a dynamic light scattering method, the virus-like particles may have substantially the same parameters (for example, a molecular weight, a mean particle size, a density, a hemagglutinin (HA) content, and the like) as the original virus particles from which the virus-like particles are derived.

For example, the virus-like particles may have a mean particle size that is 70% to 130% or 80% to 120% of a particle size of the original virus particles from which the virus-like particles are derived.

In a case where the virus-like particles are derived from influenza virus particles, a mean particle size of the virus-like particles measured by a dynamic light scattering method may be around 120 nm, 110 nm to 130 nm, or 120 nm to 130 nm. In another aspect, in a case where the virus-like particles are derived from influenza virus particles, a mean particle size of the virus-like particles measured by a dynamic light scattering method may be equal to or greater than 95 nm, equal to or greater than 100 nm, equal to or greater than 110 nm, equal to or greater than 120 nm, or equal to or greater than 130 nm. The mean particle size may be equal to or less than 145 nm, equal to or less than 140 nm, or equal to or less than 130 nm. In a case where the virus-like particles are derived from Japanese encephalitis virus particles, a mean particle size of the virus-like particles measured by a dynamic light scattering method may be around 95 nm or 80 nm to 120 nm. In a case where the virus-like particles are derived from hepatitis B virus surface antigen (HBs) particles, a mean particle size of the virus-like particles measured by a dynamic light scattering method may be around 100 nm or 90 nm to 160 nm.

In a case where the virus-like particles are measured by sucrose density gradient centrifugation, the virus-like particles may form a peak detected at a sucrose concentration of equal to or higher than 35%, a peak detected at a sucrose concentration of equal to or higher than 45% and equal to or lower than 55%, or a peak detected at a sucrose concentration of equal to or higher than 49% and equal to or lower than 52%. The sucrose concentration can be determined by a known method. For example, by placing a sample containing the virus-like particles in a density gradient consisting of layers of 15% to 60% sucrose and performing centrifugation for 16 hours at 4° C. and 18,000 rpm, the sucrose concentration can be determined.

The amount of the virus-like particles contained in a vaccine may be appropriately selected according to the type of virus or the subject of administration. For example, the amount (concentration) of the virus-like particles contained in a vaccine may be 1 to 40 μg/ml as a hemagglutinin concentration per virus strain.

The vaccine may be a monovalent vaccine containing antibodies derived from viruses or bacteria of the same kind, or may be a mixed vaccine containing antigens derived from plural kinds of viruses or bacteria. Furthermore, the vaccine may be a polyvalent vaccine containing antigens derived from plural kinds of strains of viruses or bacteria of the same family. For example, in a case where the vaccine is an influenza virus vaccine, the vaccine may contain either or both of influenza A virus-like particles and influenza B virus-like particles. The aforementioned influenza virus vaccine or the Japanese encephalitis virus vaccine may contain antigens derived from other viruses or bacteria, and may be mixed with, for example, a diphtheria•tetanus•pertussis•inactivated poliovirus mixed vaccine (DPT-IPV vaccine).

The vaccine may be formulated in the form of, for example, a liquid, powder (lyophilized powder or dried powder), a capsule, or a tablet or may be in a frozen state.

The vaccine may contain a pharmaceutically acceptable carrier. As the carrier, carriers generally used for manufacturing vaccines can be used without limitation. Specific examples thereof include saline, buffered saline, dextrose, water, glycerol, an aqueous isotonic buffer solution, and a combination of these. The vaccine may be additionally formulated with an emulsifier, a preservative (for example, thimerosal), an isotonizing agent, a pH adjuster, an inactivater (for example, formalin), and the like as appropriate.

The route of administration of the vaccine may be, for example, transdermal administration, perilingual administration, instillation administration, intradermal administration, intramuscular administration, oral administration, enteral administration, intranasal administration, intravenous administration, subcutaneous administration, intraperitoneal administration, or mouth-to-lung inhalation administration.

The vaccine may be administered by a method such as a syringe, a transdermal patch, a microneedle, an implantable slow-release device, a syringe with a microneedle, a needle-free device, or a spray.

In order to further improve the immunogenicity of the vaccine, the vaccine may contain an adjuvant together with the virus-like particles. Examples of the adjuvant include an aluminum adjuvant or an oil-in-water type suspension adjuvant containing squalene (AS03, MF59, or the like), ligands of Toll-like receptor such as CpG and 3-O-desacyl-4'-monophosphoryl lipid A (MPL), a saponin-based adjuvant, a polymer-based adjuvant such as poly-γ-glutamic acid, and polysaccharides such as chitosan and inulin.

Examples of the mammal that will become a subject include a mouse, a rat, a guinea pig, a hamster, a rabbit, a cat, a dog, a lamb, a pig, a cow, a horse, a goat, a monkey, a human being, and the like. The vaccine according to the present embodiment may be used for a human being and used for children younger than 5 years and for seniors aged 65 or over.

In a case where the vaccine is administered to a human being, the vaccine may be used such that an active component (virus-like particles) in an amount of 3.8 μg HA to 30 μg HA is administered per single dose, although the dose may vary with the purpose of administration, the administration method, and the conditions (sex, age, body weight, medical conditions, and the like) of the subject of administration.

(Method for Manufacturing Vaccine)

A method for manufacturing a vaccine containing virus-like particles according to the present embodiment includes a step of fixing particle structures of virus particles having envelopes, and a step of performing a delipidation treatment on the fixed virus particles.

As techniques for improving the safety of a vaccine, in the related art, the methods are known in which virus particles having envelopes are disrupted (splitted) using a surfactant or an organic solvent. Unfortunately, in these methods, the efficacy (immunogenicity) of the vaccine tends to decrease as the particles are broken up. In the aforementioned manufacturing method, the virus particles are fixed before the delipidation treatment is performed. Therefore, the virus particle structures are maintained even if the delipidation treatment is performed, and consequently, it is possible to improve the safety while maintaining the efficacy of the vaccine.

The manufacturing method may further include a step of culturing a host, a step of infecting the host with a virus, a step of allowing the virus to grow in the host, or a step of recovering virus particles from the host.

The virus particles may be caused to infect a host, allowed to grow, and then recovered from the host. The host may be appropriately selected according to the type of virus particles. In a case where the virus particles are influenza virus particles, examples of the host include a culture cell and a chicken egg. Examples of the culture cell include a Vero cell and an MDCK cell.

The methods for causing infection and growth of influenza virus include a method of using a chicken egg or a Vero cell as a host (Vaccine. 1998 May-June; 16 (9-10): 960-8.), a method of using a Vero cell as a host (Vaccine. 2007 Aug. 10; 25 (32): 6028-6036.), and a method of using an MDCK cell as a host (J Virol. 2012 November; 86 (22): 12341-50), and these are methods known to those in the related art.

Step of Fixing Particle Structures for Virus Particles having Envelope

In the present embodiment, "fixation" means a process of chemically binding surface antigens to each other, chemically binding a surface antigen to a matrix protein (or a membrane protein), or chemically binding matrix proteins (or membrane proteins) to each other such that the particle structures of the virus particles are maintained. The inventors of the present invention consider that, by maintaining the original particle structure of the virus, the immunogenicity of the virus-like particles may become equal to or higher than the immunogenicity of a split vaccine, and depending on the preparation conditions, the immunogenicity of the virus-like particles may become equal to or higher than the immunogenicity of inactivated whole particle viruses. Whether the particle structures are maintained can be checked by analysis using an electron microscope, sucrose density gradient centrifugation, a dynamic light scattering method, or a detection method (Slot blot, Western blot, or the like) using an anti-HA, anti-NP, or anti-M1 antibody.

Examples of the step of fixing include a method of treating virus particles with a fixative. For example, a step of adding a fixative to a suspension A containing virus particles may be performed. The type of fixative can be appropriately changed according to the type of virus. Examples of the fixative include an organic solvent, aldehydes, diimidoester, bis(3,5-dibromosalicyl)fumarate (DBBF), 1-ethyl-3-[3-dimethylaminopropyl]carbodiimide hydrochloride (EDC), and a combination of these. Examples of the organic solvent include methanol, ethanol, acetone, and a combination of these. Examples of the aldehydes include formaldehyde (for example, formalin), paraformaldehyde, glutaraldehyde, and a combination of these.

The concentration of the fixative may be appropriately changed according to the type of virus and the type of fixative. In a case where the fixative is formaldehyde, the concentration of formaldehyde may be 0.007 to 0.076 w/v % based on a total amount of the suspension A and the fixative. In a case where the concentration of formaldehyde is lower than 0.007 w/v %, the fixation becomes weak, and hence the particle structures tend not to be easily maintained. In a case where the concentration of formaldehyde is higher than 0.076 w/v %, the fixation becomes strong, and the chemical modification caused by cross-linking tends to proceed too much. From the viewpoint of further improving the HA activity, the concentration of formaldehyde may be 0.0175 to 0.076 w/v % or 0.028 to 0.076 w/v % based on a total amount of the suspension A and the fixative. The method of using the formaldehyde-containing fixative may be used in a case where the virus particles are influenza particles.

In a case where the fixative is formalin (35% to 38% aqueous formaldehyde solution), the concentration of formalin may be, based on a total amount of the suspension A and the fixative, 0.02 to 0.2 vol %, 0.05 to 0.2 vol %, or 0.08 to 0.2 vol %.

In a case where the fixative is glutaraldehyde, the concentration of glutaraldehyde may be 0.002 to 0.05 w/v % or 0.005 to 0.01 w/v % based on a total amount of the suspension A and the fixative. In a case where the concentration is lower than 0.002 w/v %, when Japanese encephalitis virus particles are used as virus particles, the particles tend to be aggregated. In a case where the concentration is higher than 0.05 w/v %, when Japanese encephalitis virus particles are used as virus particles, the epitope of an E protein, which is a main structural protein, tends to be inactivated. The method using glutaraldehyde as a fixative may be used in a case where the virus particles are influenza particles or Japanese encephalitis virus particles.

In a case where the fixative contains 1-ethyl-3-[3-dimethylaminopropyl]carbodiimide hydrochloride (EDC), the concentration of EDC may be 0.005 to 0.5 M or 0.005 to 0.05 M based on a total amount of the suspension A. The method using EDC as a fixative may be used in a case where the virus particles are influenza particles.

The temperature at the time of treating the virus particles with a fixative may be appropriately changed according to the type of virus, the type of fixative, the concentration of the fixative, and the like. The temperature may be 4° C. to 37° C. or 25° C. to 37° C.

The time period (treatment time) at the time of treating the virus particles with a fixative may be appropriately changed according to the type of virus, the type of fixative, the concentration of the fixative, the temperature of the fixing treatment, and the like. The time period may be one day to 6 weeks or 1 week to 4 weeks. In a case where EDC is used as a fixative, the time period may be 0.5 to 4 hours or 1.5 to 2.5 hours.

Step of Performing Delipidation Treatment on Fixed Virus Particles

Examples of the step of performing a delipidation treatment include a method of treating the fixed virus particles with a delipidation agent. For example, a step of adding a delipidation agent to a suspension B containing the fixed virus particles is performed. The type of delipidation agent may be appropriately changed according to the type of virus. Examples of the delipidation agent include diethyl ether, diisopropyl ether, methyl acetate, ethyl acetate, and a combination of these. The concentration at the time of treating the virus particles with a delipidation agent may be appropriately changed according to the type of virus or the type of delipidation agent. The concentration of the delipidation agent may be equal to or higher than 10 vol % and equal to or lower than 400 vol % based on a total amount of the suspension B and the delipidation agent. In a case where the concentration of the delipidation agent is lower than 10 vol %, the delipidation tends to be incomplete. In a case where the concentration of the delipidation agent is higher than 400 vol %, the structures of the virus particles tend not to be maintained. In a case where the delipidation agent is diethyl ether, the concentration of diethyl ether may be, based on a total amount of the suspension B and the delipidation agent, equal to or higher than 10 vol %, 12.5 vol % to 50 vol %, or 33 vol % to 50 vol %.

The delipidation agent may contain a surfactant, because then the aggregation of the virus-like particles is inhibited, and the yield tends to increase. Examples of the surfactant include polyoxyethylene octyl phenyl ether, polysorbate 80, and a combination of these. The concentration of the surfactant contained in the delipidation agent may be 0.002 vol % to 0.3 vol % or 0.005 vol % to 0.1 vol %.

The temperature at the time of treating the virus particles with a delipidation agent may be appropriately changed according to the type of virus, the type of delipidation agent, the concentration of the delipidation agent, and the like. The temperature may be 4° C. to room temperature (25° C.).

The time period (treatment time) at the time of treating the virus particles with a delipidation agent may be appropriately changed according to the type of virus, the type of delipidation agent, the concentration of the delipidation agent, the temperature of the delipidation treatment, and the like. The time period may be 1 hour to 2 hours.

The aforementioned manufacturing method may further include a step of removing the delipidation agent after the delipidation treatment. In a case where the delipidation agent is diethyl ether, for example, a method is performed in which a mixed solution of the suspension B and the delipidation agent is subjected to centrifugation for 5 hours at 4° C. and 3,000 rpm, and then a water phase is recovered.

If necessary, the manufacturing method may further include a step of purifying the recovered virus-like particles. The virus-like particles can be appropriately purified by a known method, and examples thereof include a filtration method using an ultrafiltration membrane.

At the time of vaccination, it is preferable that an immunogen of the same amount and the same quality as an immunogen, which is generated when an infection actually occurs, to a subject. The effect of the vaccine is determined by the mimetic properties of the immunity induced by the vaccine with respect to the immunity established by an actual infection. The vaccine may contain all of the viral proteins as antigens for a defense against an infection. The presence of a virus-derived genomic nucleic acid which is for improving the immunogenicity of a viral protein, the size and shape of virus particles, and the like affect the immune response. In this respect, the inventors of the present invention consider that the best vaccine is the one that has components and a structure closer to those of an actual virus. The virus-like particles according to the present embodiment has the same components and structure as the original virus particles except that only the lipid-component content of the virus envelope is reduced. Therefore, the virus-like particles can provide a vaccine that exhibits high immunogenicity and inhibited from causing side reactions.

EXAMPLES

Hereinafter, the present invention will be specifically described based on examples but the present invention is not limited to the examples.

Example 1

Preparation of Influenza Virus-Like Particles

1. Formalin Treatment (Step of Fixing Particle Structures of Virus Particles)

Influenza B viruses (B/Wisconsin/1/2011 strain, hereinafter, described as a "B/WC strain" in some cases) were inoculated into the chorioallantoic cavity of an 11-day old embryonated chicken egg, followed by culturing for 2 days at 34° C. The obtained chorioallantoic fluid was clarified, and then the influenza virus particles were precipitated by centrifugation. The influenza virus particles were float again on phosphate-buffered saline (PBS), and through sucrose density gradient centrifugation, a fraction with a sucrose concentration of 33% to 50% was recovered, thereby purifying the virus particles. The obtained fraction was diluted such that a final concentration of proteins of the purified influenza virus particles became 500 μg/mL, thereby obtaining a suspension A. Then, formalin (35 to 38 w/v % aqueous formaldehyde solution, fixative) was added to the suspension A such that a final concentration thereof became 0.02 to 0.2 vol % (0.007 to 0.076 w/v % in terms of formaldehyde), and the resultant was reacted for 4 weeks or 6 weeks at 4° C. or for 1 week at 25° C. After the reaction ended, the reaction solution was dialyzed using PBS such that formalin was removed, thereby obtaining a suspension B containing fixed influenza virus particles.

2. Ether Treatment (Step of Performing Delipidation Treatment on Fixed Virus Particles)

Polysorbate 80 was added to the suspension B containing the influenza virus particles treated with formalin such that a final concentration thereof became 0.1 vol %. Then, diethyl ether (delipidation agent) having the same volume as the suspension B was added thereto such that a final concentration thereof became 50 vol %, followed by stirring for 2 hours at 4° C. The obtained mixed solution was then subjected to centrifugation for 5 minutes at 4° C. and 3,000 rpm, and a water phase was recovered, thereby removing an ether phase. By the step performed as described above, influenza virus-like particles as a sample were prepared.

As a preliminary experiment, the lipid-component content of the influenza virus-like particles was measured by a cholesterol oxidase•3,5-dimethoxy-N-ethyl-N-(2-hydroxy-3-sulfopropyl)-aniline sodium (DAOS) method. As a result, the lipid-component content of the obtained influenza virus-like particles was found to be at most equal to or less than 80% by mass with respect to the lipid-component content of the influenza virus particles. Subsequently, by a fluorochrome method, the lipid-component content of the influenza virus-like particles was specifically investigated.

There is a report which states that the envelope of an influenza virus contains a large amount of cholesterol. Accordingly, cholesterol was quantified as a typical lipid component.

3. Lipid-Component Content

Among influenza A viruses, for an H1N1 subtype strain (A/California/07/2009 (X-179A) strain, hereinafter, described as an "A/CA strain" in some cases) and an H3N2 subtype strain (A/New York/39/2012 (X-233A) strain, hereinafter, described as an "A/NY strain" in some cases), virus-like particles were prepared by the method based on the aforementioned process. Furthermore, for influenza B viruses, a B/Brisbane/60/2008 strain (hereinafter, described as a "B/BR strain" in some cases) and a B/Massachusetts/2/2012 (BX-51B) strain (hereinafter, described as a "B/MA strain" in some cases), virus-like particles were prepared by the method based on the aforementioned process. Typically, a lipid-component content of influenza virus-like particles, which were reacted for 1 week at 25° C. and a formalin concentration of 0.08% and then treated with ether, was measured using an Amplex Red Cholesterol Assay Kit (manufactured by Invitrogen, trade name). First, a sample containing the influenza virus-like particles was subjected to ultracentrifugation (24,000 rpm, 2 hrs, 4° C.) such that the sample was separated into supernatant and a pellet component. The obtained pellet component was resuspended in PBS. A fluorescent substance resorufin was added to the resuspended pellet component such that a reactin occurred. By measuring fluorescence intensity of the fluorescent substance resorufin having undergone reaction, the lipid-component content of the influenza virus-like particles was quantified. As a result, the lipid-component content of the influenza virus-like particles was found to be at most equal to or less than 40% by mass with respect to the lipid-component content of whole particle influenza viruses (hereinafter, described as "whole particle antigens" in some cases) (Table 1).

TABLE 1

Ratio of cholesterol content of virus-like particles with respect to whole particle antigens (%)

| Strain name of virus particles as origin | Ratio of cholesterol content of virus-like particles (%) |
|---|---|
| A/CA strain (H1N1 subtype strain) | 39 |
| A/NY strain (H3N2 subtype strain) | 39 |
| B/MA strain (B strain) | 29 |
| B/BR strain (B strain) | 27 |

4. Lipid-Component Content (Investigating Ether Volume Ratio)

By using virus-like particles derived from the H1N1 subtype strain (A/CA strain) as a typical sample, how a change in ether volume ratio affects a delipidation treatment was investigated. First, the virus-like particles were diluted with PBS such that a final protein concentration became 2,500 μg/mL, followed by a reaction for 1 week at 25° C. and a formalin concentration of 0.08%. After the reaction ended, the reaction solution was dialyzed using PBS such that formalin was removed, thereby obtaining a suspension B containing fixed influenza virus particles. Then, an ether treatment (delipidation treatment) was performed by the same method as in "2. Ether treatment" described above except that the volume of ether was changed, thereby obtaining influenza virus-like particles. By using the obtained influenza virus-like particles, the lipid-component content was measured using an Amplex Red Cholesterol Assay Kit (manufactured by Invitrogen, trade name). The sample containing the influenza virus-like particles was subjected to ultracentrifugation (24,000 rpm, 2 hrs, 4° C.) such that the sample was separated into supernatant and a pellet component. The obtained pellet component was resuspended in PBS. A fluorescent substance resorufin was added to the resuspended pellet component such that a reaction occurred. By measuring fluorescence intensity of the fluorescent substance resorufin having undergone the reaction, the lipid-component content of the influenza virus-like particles was quantified. As a control, inactivated whole particle viruses (hereinafter, described as "whole particle antigens" in some cases) reacted for 6 week at 4° C. and a formalin concentration of 0.02% were used. As a result, in a case where the ether treatment was performed at a ratio of ether:suspension B (volume ratio) of 1:1, the lipid-component content of the influenza virus-like particles was found to be about 70% by mass with respect to the lipid-component content of the whole particle influenza viruses. In a case where the ether treatment was performed at a ratio of ether:suspension B (volume ratio) of 1:2 or 1:6, the lipid-component content of the influenza virus-like particles was about 30% by mass with respect to the lipid-component content of the whole particle influenza viruses. In contrast, in a case where the ether treatment was performed at a ratio of ether:suspension B (volume ratio) of 1:12, the lipid-component content of the influenza virus-like particles practically was not removed as in the whole particle antigens, and the content of the remaining lipid component was found to be about 100% (Table 2). Based on the above results, the inventors of the present invention consider that the effect of delipidation depends not only on the amount of ether but also on the concentration of polysorbate 80. That is, the inventors consider that as the ratio of "ether:suspension B"

changes to 1:6 from 1:1, the concentration of polysorbate 80 relatively increases, and hence delipidation proceeds. The inventors also consider that, however, when the ratio of "ether:suspension B" is 1:12, even if the concentration of polysorbate 80 is relatively high, the extremely low ether concentration exerts an influence, and hence the effect of delipidation is reduced.

TABLE 2

A/CA strain (H1N1 subtype strain): Ratio of cholesterol content of virus-like particles with respect to whole particle antigens (%)

| | Ether:suspension B (Volume ratio) | Ratio of cholesterol content (%) |
|---|---|---|
| Virus-like particles | 1:1 | 73 |
| | 1:2 | 26 |
| | 1:6 | 27 |
| | 1:12 | 103 |
| Whole particle antigens | | 100 |

Split Antigen Derived from Influenza Virus Particles

As split influenza viruses (hereinafter, described as "split antigents" in some cases) adopted as a control, an influenza HA vaccine (manufactured by The Chemo-Sero-Therapeutic Research Institute, trade name "Influenza HA vaccine "KAKETSUKEN") was used.

Example 2

Evaluation of Physical Properties

The physical properties of the virus-like particles (sample) obtained in Example 1 were evaluated by the following methods. In the following experiments, unless otherwise specified, the whole particle antigens used as a control were reacted for 6 weeks at 4° C. and a formalin concentration of 0.02%.

1. Analysis by Sucrose Density Gradient Centrifugation Method.

The virus-like particles prepared in Example 1 were analyzed by a sucrose density gradient centrifugation method. The sample was placed in a density gradient consisting of layers of 15% to 60% sucrose and subjected to centrifugation for 16 hours at 4° C. and 18,000 rpm. After the centrifugation, each fraction was fractionated in an amount of 0.6 mL, and a sucrose concentration, an HA titer, and a protein concentration of each fraction were measured. The results obtained from the H1N1 subtype strain are shown in Table 3. In the split antigens, proteins had a wide distribution within a range of sucrose concentration of 25% to 50%, and this showed that the virus particles were decomposed. In contrast, in the virus-like particles, the sample was fractionated to form a single peak at a high sucrose concentration (49% to 51.4%), and this showed that the virus-like particles had the same shape (granularity) as inactivated whole particles. The HA activity increased 2,560-fold when the formalin concentration at the time of the formalin treatment was equal to or higher than 0.02%. The results obtained from the B strain (B/WC strain) are shown in Table 4. In the split antigens, proteins had a wide distribution within a range of sucrose concentration of 25% to 50% as described above, and this showed that the virus particles were decomposed. In contrast, in the virus-like particles, the sample was fractionated to form a single peak at a high sucrose concentration (50.6% to 52.2%), and this showed that the virus-like particles had the same shape (granularity) as inactivated whole particles. Regarding the HA activity, the higher the formalin concentration at the time of the formalin treatment, the higher the HA titer. The HA titer increased 2,560-fold at a formalin concentration of 0.05%, and 5,120-fold at a formalin concentration of 0.08%.

TABLE 3

A/CA strain (H1N1 subtype strain): sucrose density gradient centrifugation analysis and HA activity in sample (virus-like particles) having undergone ether treatment and split antigens

| | Formalin treatament condition (formalin concentration, reaction temperature, and reaction time) | | | | | |
|---|---|---|---|---|---|---|
| | 0.02% 4° C. For 6 weeks | 0.02% 25° C. For 1 week | 0.05% 25° C. For 1 week | 0.08% 25° C. For 1 week | 0.2% 25° C. For 1 week | Split antigens |
| Sucrose concentration (%) | 51.3 Single peak | 51.3 Single peak | 49 Single peak | 51.4 Single peak | 50.2 Single peak | 25 to 50 Wide distribution |
| Protein content (μg/mL) | 66.6 | 62.0 | 70.8 | 70.2 | 80.2 | — |
| HA activity (x) | 2560 | 2560 | 5120 | 2560 | 2560 | — |

TABLE 4

B/WC strain (B strain): sucrose density gradient centrifugation analysis and HA activity in sample (virus-like particles) having undergone ether treatment and split antigens

| | Formalin treatament condition (formalin concentration, reaction temperature, and reaction time) | | | | | |
|---|---|---|---|---|---|---|
| | 0.02% 4° C. For 4 weeks | 0.02% 25° C. For 1 week | 0.05% 25° C. For 1 week | 0.08% 25° C. For 1 week | 0.2% 25° C. For 1 week | Split antigens |
| Sucrose concentration (%) | 50.7 Single peak | 52 Single peak | 52.2 Single peak | 50.6 Single peak | 52 Single peak | 25 to 50 Wide distribution |

TABLE 4-continued

| B/WC strain (B strain): sucrose density gradient centrifugation analysis and HA activity in sample (virus-like particles) having undergone ether treatment and split antigens | | | | | | |
|---|---|---|---|---|---|---|
| | Formalin treatament condition (formalin concentration, reaction temperature, and reaction time) | | | | | |
| | 0.02% 4° C. For 4 weeks | 0.02% 25° C. For 1 week | 0.05% 25° C. For 1 week | 0.08% 25° C. For 1 week | 0.2% 25° C. For 1 week | Split antigens |
| Protein content (μg/mL) | 83.8 | 100.0 | 110.2 | 99.2 | 101.6 | — |
| HA activity (x) | 1280 | 1280 | 2560 | 5120 | 5120 | — |

2. Analysis Using Electron Microscope

In order to more specifically investigate the shape of the virus-like particles (derived from the B/WC strain as the B strain), the virus-like particles were observed with an electron microscope. The aforementioned sample at a concentration of about 500 μg/mL was subjected to fixation for 20 minutes at room temperature by using glutaraldehyde. Then, the fixed sample was loaded on an ion-coated sheet mesh (manufactured by Nisshin EM Co., Ltd.) for observation, allowed to stand for about 60 seconds, and subjected to negative staining by using a 2% aqueous phosphotungstate solution. The stained sample was observed and imaged using a transmission electron microscope (TECNAI G2 manufactured by FEI.: acceleration voltage 120 kV)

As a typical example, a result is shown which was obtained by observing the virus-like particles that were reacted for 1 week at 25° C. and a formalin concentration of 0.05% and then treated with ether (FIG. 1(B)). As a control, a result is shown which was obtained by observing whole particle antigens that were reacted for 6 weeks at 4° C. and a formalin concentration of 0.02% (FIG. 1(A)). Furthermore, for the H1N1 subtype strain (A/CA strain) and the H3N2 subtype strain (A/NY strain), virus-like particles were prepared by the method based on the aforementioned process. In addition, for a B/BR strain and a B/MA strain as other influenza B viruses, virus-like particles were prepared by the method based on the aforementioned process. As a typical example, results are shown which were obtained by observing virus-like particles that were reacted for 1 week at 25° C. and a formalin concentration of 0.08% and then treated with ether (FIGS. 1(C) to 1(F)). The virus-like particles maintained the particle structures just like the whole particle antigens. In the observation image in which the envelopes were delipidated by the ether treatment, an aggregate formed by the bonding between the virus-like particles was not confirmed.

3. Dynamic Light Scattering

Figure 5:
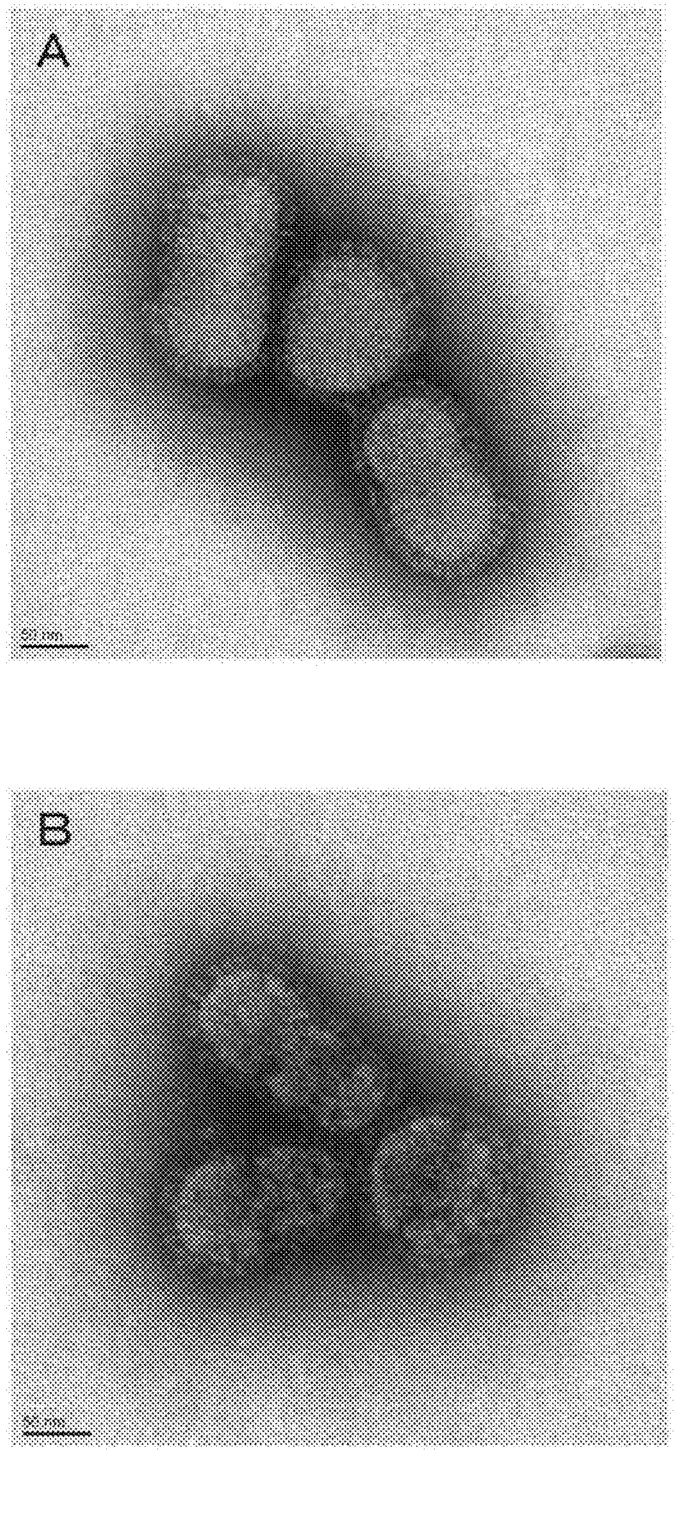
FIG. 5 shows pictures of influenza virus particles and virus-like particles derived therefrom that were taken with an electron microscope (glutaraldehyde treatment).

The mean particle size of the virus-like particles (derived from the B/WC strain as the B strain) was analyzed using a Particle Sizing System: NICOMP 380 ZLS-S. FIG. 5 shows the means particle size in a liquid determined by a dynamic light scattering method. The split antigen formed two peaks, and the peaks were confirmed at around 110 nm and 400 nm. In contrast, the mean particle size of all of other samples was confirmed at around 120 nm as a single peak. From these results, it was understood that the mean particle size obtained after the ether treatment is the same as the particle size of the virus particles. That is, it was understood that even if delipidation was performed by the ether treatment, the virus-like particles has a single mean particle size, and the mean particle size does not change. By the dynamic light scattering experiment, it was confirmed that the virus-like particles maintained the particle structures, and an impurity such as an aggregate was not observed.

TABLE 5

| B/WC strain (B strain): mean particle size in liquid determined by dynamic light scattering method | | | | | | | |
|---|---|---|---|---|---|---|---|
| | Formalin treatment condition (formalin concentration, reaction temperature, and reaction time) | | | | | | |
| | 0.02% 4° C. For 6 weeks | 0.02% 4° C. For 4 weeks | 0.02% 25° C. For 1 week | 0.05% 25° C. For 1 week | 0.08% 25° C. For 1 week | 0.2% 25° C. For 1 week | Split antigens |
| Ether treatment | − | + | + | + | + | + | |
| Volume-weighted mean particle size (nm) | 129.3 Single peak | 120.5 Single peak | 120.5 Single peak | 125.5 Single peak | 123.3 Single peak | 124.4 Single peak | 111.1 (main) 401.2 (sub) Two peaks |

4. High-Performance Liquid Chromatography (Size Exclusion Chromatography (SEC))

As a typical example, molecular weight distributions of the virus-like particles derived from the H1N1 subtype strain (A/CA strain), the whole particle antigens, and the split antigens were measured. The molecular weight distributions were measured using TS Kgel G6000PWXL (TOSOH). As an eluent, PBS was used. Table 6 shows the elution patterns. In the split antigens, 3 peaks were confirmed at around an elution time of 19 to 29 minutes. In contrast, in the virus-like particles and the whole particle antigens, a single peak was confirmed at around an elution time of 17 minutes. From these results, it was understood that the molecular weight distribution of the virus-like particles treated with ether is the same as the molecular weight distribution of the virus particles (whole particle antigens) not being treated with ether. These results showed that the virus-like particles have a single molecular weight distribution even being delipidated by the ether treatment, and the molecular weight distribution does not change.

TABLE 6

A/CA strain (H1N1 subtype strain): elution pattern of SEC

| | Virus-like particles | Whole particle antigens (formalin fixation) | Split antigens |
|---|---|---|---|
| Elution time (min) | 16 to 17<br>Single peak | 16 to 17<br>Single peak | 19, 26, 30<br>Three peaks |

5. Analysis of Viral Protein

In order to investigate the structural protein of the virus-like particles (derived from the B/WC strain as the B strain), antibody staining was performed by a Slot-blot method. For the split antigens, the sample treated only with formalin, or the sample treated with formalin and then with ether, a group (group A) obtained without performing an SDS treatment and a heating treatment on each sample and a group (group B) obtained by performing an SDS treatment and a heating treatment on each sample were prepared. Table 7 shows the type of sample.

(Western Blot Method)

For the H1N1 subtype strain (A/CA strain), virus-like particles were prepared by the method based on the aforementioned process.

Figure 3:
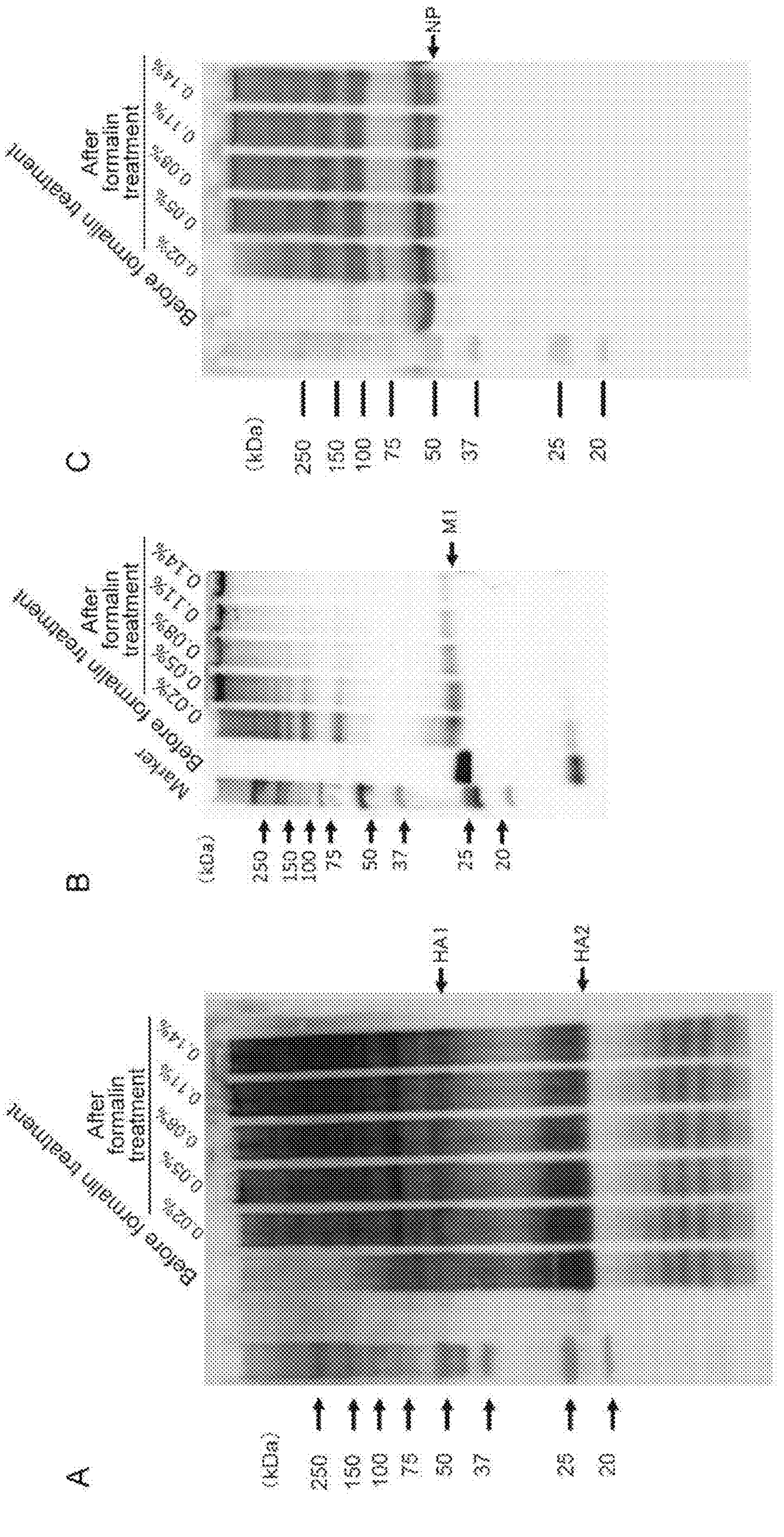
FIG. 3 shows pictures showing the results of a Western-blot method that reveals whether or not the virus-like particles derived from the influenza virus particles contain hemagglutinin (HA), a matrix protein (M1), and a nucleoprotein (NP).

The virus particles were subjected to fixation at different formaline concentrations (0.02% to 0.14%) and then treated with ether, thereby obtaining virus-like particles. The obtained virus-like particles were subjected to SDS-polyacrylamide gel electrophoresis (SDS-PAGE) and then transferred to a PVDF membrane. In the PVDF membrane, a primary antibody (a mouse monoclonal antibody: an anti-HA antibody, an anti-NP antibody, or an anti-M1 antibody) was reacted, and followed by a secondary antibody (an anti-mouse IgG-HRP conjugate), and images were taken using LAS-3000 (manufactured by FUJIFILM Corporation, trade name). At this time, RPN 2209 ECL Western Blotting Detection Reagents (manufactured by GE Healthcare, trade name) were used as a chromogenic substrate. The results of Western blot of HA (FIG. 3(A)), M1 (FIG. 3(B)), and NP (FIG. 3(C)) are shown. The results showed that, compared to the proteins not being treated with formaline, the proteins constituting each virus treated with formalin were further polymerized and migrated to the polymer side. That is, compared to the proteins not being treated with formaline, the proteins constituting each virus treated with formalin

TABLE 7

B/WC strain (B strain): type of sample

| | Sample No. (lane No.) | | | | | | |
|---|---|---|---|---|---|---|---|
| | 1 | 2 | 3 | 4 | 5 | 6 | 7 |
| Formalin treatment condition (formalin concentration, reaction temperature, and reaction time) | Split antigen | 0.02%<br>4° C.<br>For 6 weeks | 0.02%<br>4° C.<br>For 4 weeks | 0.02%<br>25° C.<br>For 1 week | 0.05%<br>25° C.<br>For 1 week | 0.08%<br>25° C.<br>For 1 week | 0.2%<br>25° C.<br>For 1 week |
| Ether treatment | + | − | + | + | + | + | + |

(Slot-Blot Method)

Each of the samples of the aforementioned groups was applied to a polyvinylidene fluoride membrane (PVDF membrane) and dried. After staining and destaining, the PVDF membrane was blocked, a primary antibody (a mouse monoclonal antibody: an anti-NP antibody or an anti-M1 antibody) was reacted, and followed by a secondary antibody (an anti-mouse IgG-HRP conjugate), and images were taken using LAS-3000 (manufactured by FUJIFILM Corporation, trade name). FIG. 2 shows the results of Slot-blot of M1 and NP. In the group (group A) in which none of the SDS treatment and the heating treatment were performed, NP and M1 were detected in the split antigens (the first lane) with destroyed particle structures and in samples (samples reacted at a formalin concentration of 0.02% and then treated with ether: the third and fourth lanes) in which formalin fixation was weak. In contrast, NP and M1 were practically not detected in the whole particle antigen (the second lane) and the samples (the fifth, sixth, and seventh lanes) with a formalin concentration of higher than 0.02%. On the other hand, in the group (group B) in which both of the SDS treatment and the heating treatment were performed, the virus-like particles were disrupted, and M1 and NP were detected in all of the samples. These results showed that M1 and NP exist in the virus-like particles.

generated a high-molecular weight polymer having a molecular weight of equal to or greater than 250 kDa at a concentration of equal to or higher than 0.05% and were found to be concentrated on top of gel. With the weak cross-link at a concentration of lower than 0.05%, particles could not be maintained at the time of ether treatment, and NP and M1 were detected as shown in FIG. 2.

6. Analysis of Genomic Nucleic Acid Derived from Virus Particles (Qualitative Analysis)

The genomic nucleic acid derived from virus particles (referred to as a "virus-derived genomic nucleic acid" in some cases) in the virus-like particles (derived from the B/WC strain as the B strain) was investigated. For the sample treated only with formalin and the sample treated with formaline and then with ether, a group obtained by performing ultracentrifugation on each sample and a group obtained without performing ultracentrifugation were prepared. By using a QIAamp Viral RNA Mini Kit (manufactured by QIAGEN, trade name), RNA was extracted from the supernatant of the aforementioned groups. After the extraction, RT-PCR was performed using a One Step RNA PCR Kit (AMV) (manufactured by TAKARA BIO INC, trade name) and a PCR System (GeneAmp R9700), thereby amplifying a DNA domain encoding HA. By performing agarose gel electrophoresis, the banding pattern of DNA products were checked.

Figure 4:
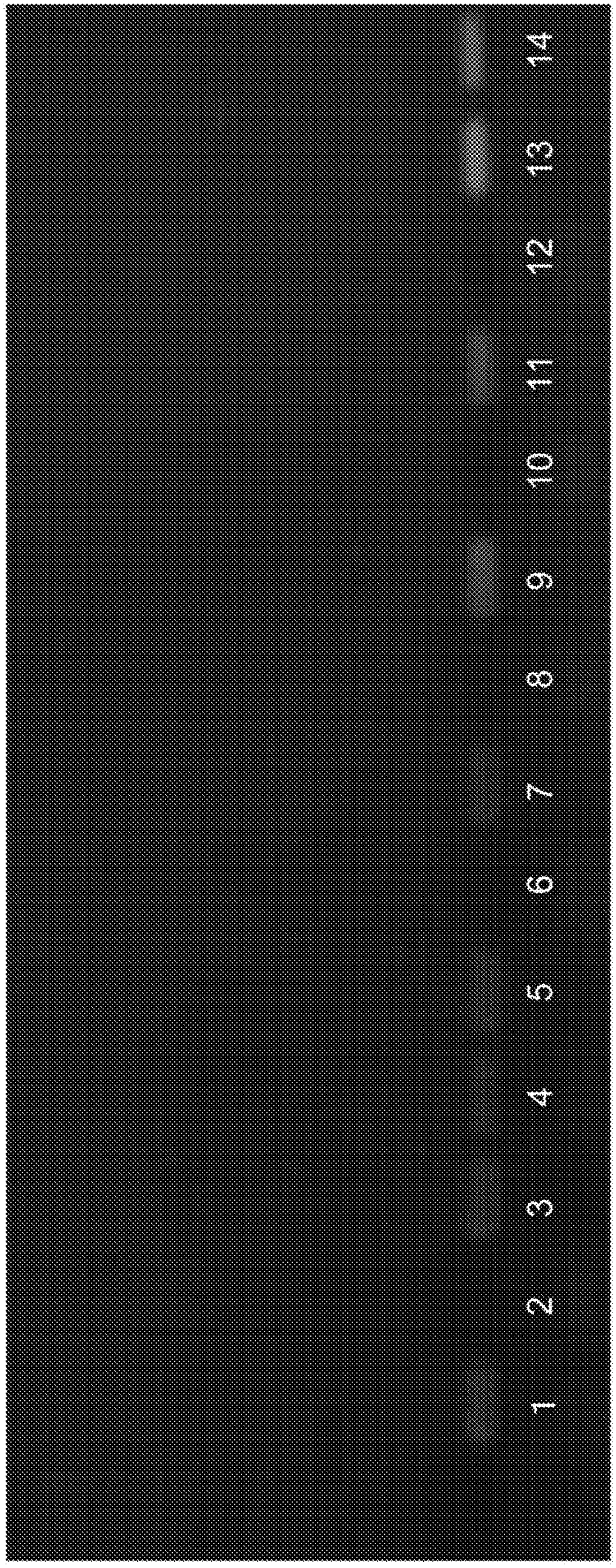
FIG. 4 shows a picture of agarose gel electrophoresis performed for checking whether or not the virus-like particles derived from the influenza virus particles contain genomic RNA.

FIG. 4 shows the results of the banding patterns of the DNA products obtained after RT-PCR. The results shown in FIG. 4 are summarized in Table 8. In a case where ultracentrifugation was not performed, virus-derived RNA was detected by RT-PCR under all conditions. In contrast, in a case where ultracentrifugation was performed, in the split antigens and the sample in which formalin fixation was the weakest (a sample reacted for 4 weeks at 4° C. and a formalin concentration of 0.02% and then treated with ether), RNA was also detected from the supernatant obtained after ultracentrifugation. In samples under conditions other than the above, RNA was not detected. These results showed that, in the antigens treated with formalin for 1 week at 25° C. and a formalin concentration of equal to or higher than 0.02% and then treated with ether, RNA is contained in the particles.

TABLE 8

B/WC strain (B strain): results of analysis of virus-derived genomic nucleic acid by RT-PCR

| | Sample No. (lane No.) | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Formalin treatment condition (formalin concentration, reaction temperature, and reaction time) | 0.02% 4° C. For 6 weeks | | 0.02% 4° C. For 4 weeks | | 0.02% 25° C. For 1 week | | 0.05% 25° C. For 1 week | | 0.08% 25° C. For 1 week | | 0.2% 25° C. For 1 week | | Split antigens | |
| Ether treatment | Not performed | | Performed | | Performed | | Performed | | Performed | | Performed | | | |
| Ultracentrifugation | − | + | − | + | − | + | − | + | − | + | − | + | − | + |
| RNA fragment | + | − | + | + | + | − | + | − | + | − | + | − | + | + |

7. Analysis of Genomic Nucleic Acid Derived from Virus Particles (Quantitative Analysis)

The genomic nucleic acid derived from virus particles (referred to as a "virus-derived genomic nucleic acid" in some cases) in virus-like particles was quantitatively investigated. The virus-like particles, the whole particle antigens, and the split antigens were diluted with PBS, and SDS and a Proteinase K were added thereto, followed by a reaction for 24 hours at 55° C. Then, by using a TRIzol LS Reagent, a PureLink RNA Mini Kit, and a PureLink DNase (manufactured by Invitrogen, trade names), RNA was extracted. The content of the extracted RNA was measured using Quant-iT RiboGreen RNA Reagent and Kit (manufactured by Invitrogen, trade name).

Table 9 shows a ratio of an RNA content of the virus-like particles and the split antigens with respect to the whole particle antigens. The ratio of RNA remaining in the virus-like particles was about 90% with respect to the whole particle antigens. In contrast, the ratio was 10% to 40% in the split antigens. These results showed that RNA practically remain in the virus-like particles.

TABLE 9

Ratio of RNA content of virus-like particles and split antigens with respect to whole particle antigens (%)

| Strain name of virus-like particles as origin | Virus-like particles | Split antigens |
|---|---|---|
| A/CA strain (H1N1 subtype strain) | 90 | 30 |
| A/NY strain (H3N2 subtype strain) | 94 | 12 |
| B/MA strain (B strain) | 87 | 22 |

TABLE 9-continued

Ratio of RNA content of virus-like particles and split antigens with respect to whole particle antigens (%)

| Strain name of virus-like particles as origin | Virus-like particles | Split antigens |
|---|---|---|
| B/BR strain (B strain) | 93 | 38 |

8. Immunogenicity 1

Regarding the influenza A virus, virus-like particles were prepared for the H3N2 subtype strain (A/Texas/50/2012 (X-223) strain, hereinafter, described as an "A/TX strain" in some cases) by the method based on Example 1. The immunogenicity of the virus-like particles was evaluated using mice. ddY mice (females, 8-week-old) were inoculated with the split antigens, whole particle antigens, or the virus-like particles by intramuscular administration at an inoculum amount of 0.8 μg in terms of a protein amount (16 mice per group). Three weeks after immunization, the mice were euthanized and subjected to collection of whole blood. A serum was obtained through centrifugation, and an HI antibody titer was measured. As a typical example, the results of the immunogenicity (HI antibody titer (GMT)) of samples, which were reacted for 1 week at 25° C. and a formalin concentration of 0.08% and then treated with ether, are shown in Table 10. In a case of the H1N1 subtype strain or the H3N2 subtype strain, the immunogenicity of the virus-like particles was significantly higher (H1N1 subtype strain: $P<0.05$, H3N2 subtype strain: $P<0.01$) than that of the split antigens and equal to that of the whole particle antigens. In a case of the B strain (B/MA strain), the immunogenicity of the virus-like particles was higher than that of the split antigens and equal to that of the whole particle antigens.

TABLE 10

Results of immunogenicity (HI antibody titer (GMT))

| Strain name of virus particles as origin | Split antigens | Whole particle antigens | Virus-like particles |
|---|---|---|---|
| A/CA strain (H1N1 subtype strain) | 12 | 44 | 35 |
| A/TX strain (H3N2 subtype strain) | 73 | 99 | 153 |
| B/MA strain (B strain) | 31 | 46 | 40 |

9. Immunogenicity 2

For the H1N1 subtype strain (A/New Caledonia/20/99, hereinafter, described as an "A/NC strain" in some cases), the H3N2 subtype strain (A/Wyoming/3/2003, hereinafter, described as an "A/WY strain" in some cases), and the B strain (B/Shanghai/361/2002, hereinafter, described as a "B/SG strain" in some cases), virus-like particles were prepared by the method based on Example 1. The immunogenicity of the obtained influenza virus-like particles was evaluated using mice. ddY mice (females, 8-week-old), 8 mice per group, were inoculated twice with the split antigens or the virus-like particles at an inoculum amount of 1 μg HA by subcutaneous administration at an interval of 3 weeks. Three weeks after the primary immunization, collection of whole blood was performed, and 2 weeks after the secondary immunization, collection of whole blood was performed again. A serum was obtained through centrifugation, and an HI antibody titer was measured. As a typical example, the results of the immunogenicity (HI antibody titer (GMT)) of the samples, which were reacted for 3 days at 5° C. and a formalin concentration of 0.2% and then treated with ether, are shown in Table 11 (after primary immunization) and Table 12 (after secondary immunization). In a case of the A/NC strain or the A/WY strain after the primary immunization, the immunogenicity of the virus-like particles was significantly higher than that of the split antigens.

TABLE 11

Results of immunigenicity (HI antibody titer (GMT) (after primary immunization))

| Strain name of virus particles as origin | Split antigens | Virus-like particles |
|---|---|---|
| A/NC strain (H1N1 subtype strain) | 34 | 123*1 |
| A/WY strain (H3N2 subtype strain) | 31 | 207*2 |
| B/SG strain (B strain) | 52 | 95 |

*1P < 0.05,
*2P < 0.01

TABLE 12

Results of immunogenicity (HI antibody titer (GMT) (after secondary immunization))

| Strain name of virus particles as origin | Split antigens | Virus-like particles |
|---|---|---|
| A/NC strain (H1N1 subtype strain) | 174 | 293 |
| A/WY strain (H3N2 subtype strain) | 207 | 349 |
| B/SG strain (B strain) | 131 | 238 |

10. Immunogenicity 3

The immunogenicity of split antigens, whole particle antigens, and virus-like particles was evaluated using crab-eating macaques (females, 21- to 29-month-old). The crab-eating macaques, 5 monkeys per group, were inoculated twice with the split antigens, the whole particle antigens, or the virus-like particles by subcutaneous administration at an inoculum amount corresponding to 7.5 μg HA (a protein mass corresponding to an HA amount of the split antigens) at an interval of 28 days. Before the secondary immunization and 28 days after the secondary immunization, partial blood collection was performed. A serum was obtained through centrifugation, and an HI antibody titer and a neutralizing antibody titer were measured. As a typical example, the results of the immunogenicity of the samples (virus-like particles), which were reacted for 7 days at 25° C. in 0.08% formalin and then treated with ether, are shown in Table 13 (HI antibody titer (GMT) after secondary immunization) and Table 14 (neutralizing antibody titer (GMT) after secondary immunization). From the HI antibody titer, it was understood that the immunogenicity of the virus-like particles is higher than that of the split antigens. Particularly, in the H1N1 subtype strain, the immunogenicity was significantly high. It was understood that, in the neutralizing antibody titer, the immunogenicity of the virus-like particles is higher than that of the split antigens. Particularly, in the H1N1 subtype strain and the B strain, the immunogenicity was significantly high.

TABLE 13

HI antibody titer (GMT) after secondary immunization

| Strain name of virus particles as origin | Split antigens | Whole particle antigens | Virus-like particles |
|---|---|---|---|
| A/CA strain (H1N1 subtype strain) | 10 | 46*1 | 35*1 |
| A/TX strain (H3N2 subtype strain) | 9 | 53*2 | 23 |
| B/MA strain (B strain) | 5 | 17*1 | 7 |

*1P < 0.05,
*2P < 0.01

TABLE 14

Neutralizing antibody titer (GMT) after secondary immunization

| Strain name of virus particles as origin | Split antigens | Whole particle antigens | Virus-like particles |
|---|---|---|---|
| A/CA strain (H1N1 subtype strain) | 61 | 557 | 640*1 |
| A/TX strain (H3N2 subtype strain) | 53 | 368*1 | 184 |
| B/MA strain (B strain) | 15 | 211*2 | 70*1 |

*1P < 0.05,
*2P < 0.01

11. Antibody Subclass Analysis 1

As antibody subclass analysis, antibody titers of IgG1 and IgG2a specific to a viral antigen that were contained in the mouse serum obtained in "8. Immunogenicity 1" described above were measured. As a control, mice were immunized in the same manner as described above with samples which were reacted for 1 week at 25° C. in 0.02% formalin and then treated with ether. The antibody titers of IgG1 and IgG2a specific to a viral antigen that were contained in the obtained mouse serum were measured. As a result, it was found that, contrary to the split antigens, the virus-like particles (formalin concentration: 0.08%) induce more antigen-specific IgG2a than antigen-specific IgG1 just like the whole particle antigens. In contrast, it was found that, among the same virus-like particles, the sample fixed using 0.02% formalin induces antigen-specific IgG1 more than antigen-specific IgG2a just like the split antigens (Tables 15 to 17). The antibody of the IgG2a subclass induced by the Th1 response has a better defensive ability against an infection caused by influenza viruses compared to the antibody of the IgG1 subclass induced by the Th2 response. Therefore, the efficacy of the virus-like particles (formalin concentration: 0.08%) could be further improved.

TABLE 15

A/CA strain (H1N1 subtype strain): results of subclass analysis (EU/mL)

| IgG subclass | Split antigens | Whole particle antigens | Virus-like particles 0.08% | Virus-like particles 0.02% |
|---|---|---|---|---|
| IgG1 | 4815 | 451 | 2951 | 8977 |
| IgG2a | 1947 | 52209 | 19894 | 5376 |

The value obtained when each mouse serum immunized with the split vaccine was diluted 25,600x was regarded as 1 EU/mL.

TABLE 16

A/TX strain (H3N2 subtype strain): results of subclass analysis (EU/mL)

| IgG subclass | Split antigens | Whole particle antigens | Virus-like particles 0.08% | Virus-like particles 0.02% |
|---|---|---|---|---|
| IgG1 | 7550 | 407 | 10209 | 10679 |
| IgG2a | 3808 | 12326 | 15961 | 3707 |

The value obtained when each mouse serum immunized with the split vaccine was diluted 25,600x (IgG1) or 51,200x (IgG2a) was regarded as 1 EU/mL.

TABLE 17

B/MA strain (B strain): results of subclass analysis (EU/mL)

| IgG subclass | Split antigens | Whole particle antigens | Virus-like particles 0.08% | Virus-like particles 0.02% |
|---|---|---|---|---|
| IgG1 | 15838 | 308 | 3859 | 9734 |
| IgG2a | 3020 | 26074 | 52923 | 10464 |

The value obtained when each mouse serum immunized with the split vaccine was diluted 25,600x was regarded as 1 EU/mL.

12. Immunogenicity 4

In order to analyze the mechanism of immunogenicity of the virus-like particle antigens, Toll like receptor 7 knock-out (TLR7KO) mice (Backborne: BALB/c) were used. The used mice were purchased from Oriental Bioservice, Inc. The mice (females, 5-week-old), 5 to 6 mice per group, were inoculated twice with the whole particle antigens, the virus-like particle antigens, or the split antigens at an inoculum amount of 2 μg/strain in terms of a protein amount by intramuscular administration at an interval of 3 weeks. Three weeks after the primary immunization, partial blood collection was performed, and 2 weeks after the secondary immunization, collection of whole blood was performed. A serum was obtained through centrifugation, and an HI antibody titer was measured. As vaccine strains, the H1N1 subtype strain (A/CA strain), the H3N2 subtype strain (A/NY strain), and the B strain (B/BR strain and the B/MA strain) were used. The whole particle antigens, the virus-like particle antigens, and the split antigens were prepared by the method based on Example 1. Table 18 shows a geometric mean titer (GMT) of the HI antibody titer in the serum obtained 3 weeks after the primary immunization. In a wild-type mouse (+/+), the virus-like particles had an HI antibody titer higher than that of the split antigens. In contrast, in the knock-out mouse (−/−), the HI antibody titer of the virus-like particles was reduced and became equal to the HI antibody titer of the split antigens. These results showed that the single-stranded viral RNA contained in the virus-like particles makes a great contribution to the immunogenicity of the virus-like particles.

TABLE 18

Results of immunogenicity (HI antibody titer (GMT))

| Strain name of virus particles as origin | TLR7 | Split antigens | Whole particle antigens | Virus-like particles |
|---|---|---|---|---|
| A/CA strain | +/+ | 17.4 | 30.3 | 25.2 |
| (H1N1 subtype strain) | −/− | 6.6 | 7.6 | 6.6 |

13. Antibody Subclass Analysis 2

As antibody subclass analysis, the antibody titers of IgG1 and IgG2a specific to a viral antigen that were contained in the mouse serum obtained in "12. Immunogenicity 4" described above were measured. The results are shown in Tables 19 to 21. In the BALB/c wild-type mouse (+/+) in which the immune response predominated by Th2 is easily induced, the virus-like particles were also found to induce the antigen-specific IgG2a more than the antigen-specific IgG1 contrary to the split antigens. In contrast, in the knock-out mouse (−/−), the antibody titer of IgG2a was markedly reduced. These results showed that the single-stranded viral RNA is essential for inducing the immunity predominated by Th1.

TABLE 19

A/CA strain (H1N1 subtype strain): results of subclass analysis (EU/mL)

| TLR7 | IgG subclass | Split antigens | Whole particle antigens | Virus-like particles |
|---|---|---|---|---|
| +/+ | IgG1 | 3142 | 269 | 1496 |
| | IgG2a | 2147 | 11585 | 10980 |
| −/− | IgG1 | 1425 | 271 | 1237 |
| | IgG2a | 200 | 2407 | 1121 |

The value obtained when each mouse serum immunized with the split vaccine was diluted 25,600x was regarded as 1 EU/mL.

TABLE 20

A/NY strain (H3N2 subtype strain): results of subclass analysis (EU/mL)

| TLR7 | IgG subclass | Split antigens | Whole particle antigens | Virus-like particles |
|---|---|---|---|---|
| +/+ | IgG1 | 970 | 200 | 358 |
| | IgG2a | 944 | 10712 | 5759 |
| −/− | IgG1 | 359 | 200 | 448 |
| | IgG2a | 200 | 1336 | 608 |

The value obtained when each mouse serum immunized with the split vaccine was diluted 25,600x was regarded as 1 EU/mL.

TABLE 21

B/MA strain (B strain): results of subclass analysis (EU/mL)

| TLR7 | IgG subclass | Split antigens | Whole particle antigens | Virus-like particles |
|---|---|---|---|---|
| +/+ | IgG1 | 390 | 200 | 444 |
| | IgG2a | 544 | 8621 | 2625 |

TABLE 21-continued

| B/MA strain (B strain): results of subclass analysis (EU/mL) | | | | |
|---|---|---|---|---|
| TLR7 | IgG subclass | Split antigens | Whole particle antigens | Virus-like particles |
| −/− | IgG1 | 200 | 392 | 913 |
| | IgG2a | 200 | 2036 | 417 |

The value obtained when each mouse serum immunized with the split vaccine was diluted 25,600x was regarded as 1 EU/mL.

14. Analysis of Number of IFN-γ Producing Cells

In order to measure the number of antigen-specific IFN-γ producing cells that were contained in the spleen of the mouse obtained in "12 Immunogenicity 4" described above, ELISPOT assay was performed. The analysis was performed using Mouse IFN gamma ELISPOT Ready-SET-Go! (manufactured by eBioscience, trade name) based on the method described in the attached manual. The results are shown in Tables 22 to 25. It was confirmed that IFN-γ, which is produced from cells such as dendritic cells, Th1 cells, and NK cells involved in the cellular immunity, was more strongly induced in the mouse inoculated with the whole particle antigens or the virus-like particles than in the mouse inoculated with the split antigens. In the knock-out mouse (−/−), the number of IFN-γ producing cells induced by the virus-like particle antigens were markedly reduced. These results showed that the IFN-γ producing cells are induced by the single-stranded viral RNA, and the immune response predominated by Th1 cells is induced.

TABLE 22

| A/CA strain (H1N1 subtype strain): Number of antigen-specific IFN-γ producing cells (in 1 × $10^6$ splenocytes) | | | |
|---|---|---|---|
| TLR7 | Split antigens | Whole particle antigens | Virus-like particles |
| +/+ | 12 | 142 | 83 |
| −/− | 4 | 52 | 5 |

TABLE 23

| A/NY strain (H3N2 subtype strain): Number of antigen-specific IFN-γ producing cells (in 1 × $10^6$ splenocytes) | | | |
|---|---|---|---|
| TLR7 | Split antigens | Whole particle antigens | Virus-like particles |
| +/+ | 10 | 95 | 58 |
| −/− | 4 | 40 | 4 |

TABLE 24

| B/MA strain (B strain): Number of antigen-specific IFN-γ producing cells (in 1 × $10^6$ splenocytes) | | | |
|---|---|---|---|
| TLR7 | Split antigens | Whole particle antigens | Virus-like particles |
| +/+ | 10 | 57 | 52 |
| −/− | 6 | 49 | 5 |

TABLE 25

| B/BR strain (B strain): Number of antigen-specific IFN-γ producing cells (in 1 × $10^6$ splenocytes) | | | |
|---|---|---|---|
| TLR7 | Split antigens | Whole particle antigens | Virus-like particles |
| +/+ | 4 | 43 | 47 |
| −/− | 8 | 38 | 3 |

15. Analysis of Number of Memory B Cells

In order to measure the number of antigen-specific memory B cells contained in the mouse spleen obtained in "12 Immunogenicity 4" described above, ELISPOT assay was performed. Before ELISPOT was performed, in order for antibody producing cells to be differentiated from the memory B cells, the cells were stimulated with mitogens (lectin derived from *Phytolacca americana*, Protein A soluble derived from *S. aureus*, CpG ODN, and LPS derived from *Escherichia coli*). The results are shown in Tables 26 to 29. It was confirmed that the memory B cells in the splenocytes are more strongly induced in the mouse inoculated with the whole particle antigens or the virus-like particles than in the mouse inoculated with the split antigens. In the knock-out mouse (−/−) inoculated with the virus-like particle antigens, the number of memory B cells in the spleen was reduced. These results showed that the single-stranded viral RNA is strongly involved in the memory B cell inducing ability of the virus-like particle antigens.

TABLE 26

| A/CA strain (H1N1 subtype strain): Number of antigen-specific memory B cells (in 1 × $10^6$ splenocytes) | | | |
|---|---|---|---|
| TLR7 | Split antigens | Whole particle antigens | Virus-like particles |
| +/+ | 48 | 126 | 117 |
| −/− | 48 | 98 | 55 |

TABLE 27

| A/NY strain (H3N2 subtype strain): Number of antigen-specific memory B cells (in 1 × $10^6$ splenocytes) | | | |
|---|---|---|---|
| TLR7 | Split antigens | Whole particle antigens | Virus-like particles |
| +/+ | 45 | 123 | 115 |
| −/− | 50 | 85 | 48 |

TABLE 28

| B/MA strain (B strain): Number of antigen-specific memory B cells (in 1 × $10^6$ splenocytes) | | | |
|---|---|---|---|
| TLR7 | Split antigens | Whole particle antigens | Virus-like particles |
| +/+ | 30 | 45 | 62 |
| −/− | 18 | 33 | 30 |

TABLE 29

| B/BR strain (B strain): Number of antigen-specific memory B cells (in 1 × $10^6$ splenocytes) | | | |
|---|---|---|---|
| TLR7 | Split antigens | Whole particle antigens | Virus-like particles |
| +/+ | 48 | 65 | 85 |
| −/− | 18 | 63 | 18 |

16. Fever Test 1

The split antigens, the whole particle antigens, or the virus-like particles were diluted with PBS such that a protein content in 1 mL of the antigens became 240 μg, thereby obtaining a sample. As a typical example for the virus-like particles, a sample reacted for 1 week at 25° C. in 0.08% formalin and then treated with ether was used. Rabbits were inoculated with the sample at a dose of 1 mL/1 kg (body weight), and an increase of rectal temperature caused by fever was observed. Table 30 shows the total increase of rectal temperature (° C.) in three rabbit caused by a febrile reaction.

Only in the whole particle antigens not being treated with ether, a total of equal to or higher than 1.3° C. of the increase of rectal temperature caused by fever was confirmed. In none of the split antigens treated with ether and the virus-like particles, a total of equal to or higher than 1.3° C. of the increase of rectal temperature caused by fever was not confirmed.

TABLE 30

| Total increase of rectal temperature in three rabbits caued by febrile reaction (° C.) | | | |
|---|---|---|---|
| Strain name of virus particles as origin | Split antigens | Whole particle antigens | Virus-like particles |
| A/CA strain (H1N1 subtype strain) | 0.53 | 3.72 | 0.63 |
| A/TX strain (H3N2 subtype strain) | 0.20 | 1.72 | 0.28 |
| B/MA strain (B strain) | 0.33 | 3.99 | 0.12 |

17. Fever Test 2

The virus particles of the H1N1 subtype strain (A/CA strain) were diluted such that a final protein concentration thereof became 2,500 μg/mL and reacted for 1 week at 25° C. in 0.08% formalin. After the reaction ended, the reaction solution was dialyzed using PBS such that formalin was removed, thereby obtaining a suspension B containing fixed influenza virus particles. Then, an ether treatment was performed by the same method as in "2. Ether treatment" described above, except that the ether volume and the concentration of the polysorbate 80 were changed to 0.05 vol %, thereby obtaining influenza virus-like particles having different cholesterol contents. The obtained influenza virus-like particles were diluted with PBS such that a protein content in 1 mL of the particles became 240 μg, thereby obtaining a sample. Rabbits were inoculated with the sample at a dose of 1 mL/1 kg (body weight), and an increase of rectal temperature caused by fever was observed. Table 31 shows the total increase of rectal temperature (° C.) in three rabbit caused by a febrile reaction.

In all of the samples including the virus-like particles (sample in which a ratio of ether:suspension B (volume ratio) was 1:1) in which the content of remaining cholesterol was about 70% with respect to the whole particle antigens, a total of equal to or higher than 1.3° C. of the increase of rectal temperature caused by fever was not confirmed.

TABLE 31

| A/CA strain (H1N1 subtype strain): Total increase of rectal temperature in three rabbits inoculated with virus-like particles caused by febrile reaction (° C.) | |
|---|---|
| Ether:suspension B (volume ratio) | Total increase of rectal temperature caused by febrile reaction |
| 1:1 | 0.27 |
| 1:2 | 0.08 |
| 1:6 | 0.71 |

18. Cytokine Quantification 1

As a method alternative to the fever test, the amount of cytokine was evaluated using an inflammatory cytokine measurement system using human PBMC. The amount of cytokine was measured for IL-1β and IL-6 which are typical inflammatory cytokines. The human peripheral blood mononuclear cells (PBMC) were suspended in FCS containing MEM medium and diluted at $4\times10^6$ cells/mL. The cells were added in an amount of 100 μL to a 96-well plate, and the split antigens, the whole particle antigens, or the virus-like particles were added thereto in the same amount (final concentration: 50 μg/mL). Then, the cells were cultured for 24 hours at 37° C. in a $CO_2$ atmosphere, and IL-1β and IL-6 in the supernatant were quantified by an ELISA method. As a typical example, the results of quantification of the cytokine (IL-1β) of the sample, which was reacted for 1 week at 25° C. in 0.08% formalin and then treated with ether, are shown in Table 32, and the results of quantification of the cytokine (IL-6) of the same sample are shown in Table 33. It was understood that, in a case where the virus-like particles are used, the amount of inflammatory cytokines becomes smaller than in a case where the whole particle antigens are used. This result showed that side reactions are more easily suppressed in the virus-like particles than in the whole particle antigens.

TABLE 32

| Results of cytokine quantification (IL-1β) (pg/mL) | | | |
|---|---|---|---|
| Strain name of virus particles as origin | Split antigens | Whole particle antigens | Virus-like particles |
| A/CA strain (H1N1 subtype strain) | 3.3 | 44.5 | 6.4 |
| A/TX strain (H3N2 subtype strain) | 5.1 | 13.0 | 5.5 |
| B/MA strain (B strain) | 7.3 | 7.8 | 7.3 |

TABLE 33

| Results of cytokine quantification (IL-6) (pg/mL) | | | |
|---|---|---|---|
| Strain name of virus particles as origin | Split antigens | Whole particle antigens | Virus-like particles |
| A/CA strain (H1N1 subtype strain) | 18.4 | 205.1 | 52.3 |
| A/TX strain (H3N2 subtype strain) | 29.5 | 118.6 | 36.5 |
| B/MA strain (B strain) | 35.1 | 165.4 | 58.2 |

Example 3

Preparation of Influenza Virus-Like Particles

1. Glutaraldehyde (GA) Treatment (Step of Fixing Virus Particles Through Irreversible Cross-Linking Reaction without Forming Methylene Cross-Link as in Formalin)

Influenza A viruses (H3N2 subtype strain (A/NY strain)) and influenza B viruses (B/BR strain) were purified in the same manner as in Example 1. The purified influenza virus particles were inactivated using β-propiolactone (BPL) and then diluted such that a final protein concentration thereof became 1,000 μg/mL, thereby obtaining a suspension A1 (A/NY strain) and a suspension A2 (B/BR strain). Then, a 1 w/v % GA solution was diluted such that a GA concentration thereof became 0.016 w/v % or 0.008 w/v %.

The suspension A1 or the suspension A2 were mixed with the diluted GA solution (0.016 w/v % or 0.008 w/v %) in an equal amount, followed by a reaction for 3 days at 4° C. After the reaction ended, the reaction solution was dialyzed using PBS such that GA was removed, thereby obtaining a suspension B1 (A/NY strain) and a suspension B2 (B/BR strain) containing fixed influenza virus particles (whole particle antigens (GA fixation)).

2. Ether Treatment (Step of Performing Delipidation Treatment on Fixed Virus Particles)

Polysorbate 80 was added to the suspension B1 and the suspension B2 containing the influenza virus particles treated with GA such that a final concentration thereof became 0.05 vol %. Then, diethyl ether (delipidation agent) was added to the suspension B1 or the suspension B2 such that a final concentration thereof became 33 vol %, followed by stirring for 1 hour at 25° C. The obtained mixed solution was then subjected to centrifugation for 5 minutes at 4° C. and 3,000 rpm, and a water phase was recovered, thereby removing an ether phase. Through the aforementioned step, influenza virus-like particles as a sample were prepared.

The lipid-component content of the obtained influenza virus-like particles was measured using an Amplex Red Cholesterol Assay Kit (manufactured by Invitrogen, trade name). The sample containing the influenza virus-like particles was subjected to ultracentrifugation (24,000 rpm, 2 hrs, 4° C.) such that the sample was separated into supernatant and a pellet component. The obtained pellet component was resuspended in PBS. A fluorescent substance resorufin was added to the resuspended pellet component such that a reaction occurred. By measuring fluorescence intensity of the fluorescent substance resorufin having undergone the reaction, the lipid-component content of the influenza virus-like particles with respect to the whole particle antigens (GA fixation) was quantified. As a result, it was confirmed that, the lipid-component content of the influenza virus-like particles is at most equal to or less than 50% by mass with respect to the lipid-component content of the influenza virus particles (Table 34).

TABLE 34

Ratio of cholesterol content of virus-like particles with respect to whole particle antigens (%)

| Strain name of virus particles as origin | GA concentration (w/v %) | Ratio of cholesterol content of virus-like particles |
|---|---|---|
| A/NY strain | 0.004 | 28 |
| (H3N2 subtype strain) | 0.008 | 50 |
| B/BR strain | 0.004 | 12 |
| (B strain) | 0.008 | 23 |

Example 4

Evaluation of Physical Properties

The physical properties of the virus-like particles (sample) obtained in Example 3 were evaluated by the following methods.

1. Analysis Using Electron Microscope

In order to more specifically investigate the shape of the virus-like particles (derived from the A/NY strain), the virus-like particles were observed with an electron microscope. The aforementioned sample at a concentration of about 500 μg/mL was subjected to fixation for 20 minutes at room temperature by using glutaraldehyde. Then, the fixed sample was loaded on an ion-coated sheet mesh (manufactured by Nisshin EM Co., Ltd.) for observation, allowed to stand for about 60 seconds, and subjected to negative staining by using a 2% aqueous phosphotungstate solution. The stained sample was observed and imaged using a transmission electron microscope (TECNAI G2 manufactured by FEI.: acceleration voltage 120 kV)

As a typical example, a result is shown which was obtained by observing the virus-like particles that were reacted for 3 days at 4° C. at a GA concentration of 0.008 w/v % and then treated with ether (FIG. 5(B)). As a control, a result is shown which was obtained by observing whole particle antigens that were reacted for 3 days at 4° C. at a GA concentration of 0.008 w/v % (FIG. 5(A)). The virus-like particles maintained the particle structures just like the whole particle antigens. In the observation image in which the envelopes were destroyed by the ether treatment, an aggregate formed by the bonding between the virus-like particles was not observed.

2. Dynamic Light Scattering

The mean particle size of the virus-like particles was analyzed using Zetasizer Nano ZS (manufactured by Malvern Instruments Ltd). Table 35 shows the mean particle size in a liquid determined by a dynamic light scattering method. The mean particle size of the virus-like particles was about 130 nm appeared as a single peak. From this results, it was understood that the mean particle size obtained after the ether treatment is the same as the particle size of the virus particles. That is, it was understood that even if delipidation was performed by the ether treatment, the virus-like particles has a single mean particle size, and the mean particle size does not change. From the dynamic light scattering experiment, it was confirmed that the virus-like particles maintain the particle structures, and an impurity such as an aggregate was not observed.

TABLE 35

Mean particle size in liquid determined by dynamic light scattering method (volume-weighted means particle size (main peak) (nm))

| Strain name of virus particles as origin | GA concentration (w/v %) | Virus-like particles | Whole particle antigens (formalin fixation) |
|---|---|---|---|
| A/NY strain | 0.004 | 141.7 | 142.6 |
| (H3N2 subtype strain) | 0.008 | 144.6 | |
| B/BR strain | 0.004 | 132.2 | 136.6 |
| (B strain) | 0.008 | 133.0 | |

The whole particle antigens (formalin fixation) were reacted for 6 weeks at 4° C. at a formalin concentration of 0.02%.

3. Analysis of Genomic Nucleic Acid Derived from Virus Particles (Quantitative Analysis)

The genomic nucleic acid derived from virus particles (referred to as a "virus-derived genomic nucleic acid" in some cases) in virus-like particles was quantitatively investigated. The virus-like particles and the whole particle antigens were diluted with PBS, and SDS and a Proteinase K were added thereto, followed by a reaction for 18 to 57 hours at 55° C. Then, by using a TRIzol LS Reagent, a PureLink RNA Mini Kit, and a PureLink DNase (manufactured by Invitrogen, trade names), RNA was extracted. The content of the extracted RNA was measured using Quant-iT RiboGreen RNA Reagent and Kit (manufactured by Invitrogen, trade name).

Table 36 shows a ratio of an RNA content of the virus-like particles with respect to the whole particle antigens. The ratio of RNA remaining in the virus-like particles was about 80% with respect to the whole particle antigens. This result showed that RNA practically remains in the virus-like particles as in the case of formalin treatment, even in a case of GA treatment.

TABLE 36

Ratio of RNA content of virus-like particles with respect to whole particle antigens (%)

| Strain name of virus particles as origin | GA concentration (w/v %) | Ratio of RNA content of virus-like particles |
|---|---|---|
| A/NY strain | 0.004 | 83 |
| (H3N2 subtype strain) | 0.008 | 100 |
| B/BR strain | 0.004 | 100 |
| (B strain) | 0.008 | 100 |

4. Immunogenicity 1

The immunogenicity of the virus-like particles was evaluated using mice. ddY mice (females, 8-week-old) were inoculated with the split antigens (formalin inactivation) or the virus-like particles by intramuscular administration at an inoculum amount of 0.8 μg in terms of a protein amount (16 mice per group). Three weeks after immunization, the mice were euthanized and subjected to collection of whole blood. A serum was obtained through centrifugation, and a neutralizing antibody titer was measured. As a typical example, the results of the immunogenicity (neutralizing antibody titer (GMT)) of samples, which were reacted for 3 days at 4° C. in 0.004 w/v % GA concentration and then treated with ether, are shown in Table 37. In a case of the B strain, the immunogenicity of the virus-like particles was higher than that of the split antigens.

TABLE 37

Results of immunogenicity (neutralizing antibody titer (GMT))

| Strain name of virus particles as origin | Split antigens | Virus-like particles |
|---|---|---|
| B/BR strain (B strain) | 27 | 48 |

5. Immunogenicity 2

For the B/WC strain as the B strain, virus-like particles were prepared by the method based on Example 1. The immunogenicity of the obtained influenza virus-like particles was evaluated using mice. ddY mice (females, 8-week-old) were inoculated with the split antigens (formalin inactivation) or the virus-like particles by intramuscular administration at an inoculum amount of 0.8 μg in terms of a protein amount (16 mice per group). Three weeks after immunization, the mice were euthanized and subjected to collection of whole blood. A serum was obtained through centrifugation, and an HI antibody titer was measured. As a typical example, the results of the immunogenicity (HI antibody titer (GMT)) of virus-like particles, which were reacted for 3 days at 4° C. in 0.010 w/v % GA and then treated with ether, are shown in Table 38. The immunogenicity of the virus-like particles was higher than that of the split antigens.

TABLE 38

Results of immunogenicity (HI antibody titer (GMT))

| Strain name of virus particles as origin | Split antigens | Virus-like particles |
|---|---|---|
| B/WC strain (B strain) | 17 | 25 |

6. Fever Test

The virus-like particles were diluted with PBS such that a protein content in 1 mL of the particles became 240 μg, thereby obtaining a sample. Rabbits were inoculated with the sample at a dose of 1 mL/1 kg (body weight), and an increase of rectal temperature caused by fever was observed. Table 39 shows the total increase of rectal temperature (° C.) in three rabbit caused by a febrile reaction.

In none of the virus-like particles treated with ether, a total of equal to or higher than 1.3° C. of the increase of rectal temperature caused by fever was not confirmed.

TABLE 39

Total increase of rectal temperature in three rabbits inoculated with virus-like particles caused by febrile reaction (° C.)

| Strain name of virus particles as origin | GA concentration (w/v %) | Total increase of rectal temperature caused by febrile reaction (° C.) |
|---|---|---|
| A/NY strain | 0.004 | 0.47 |
| (H3N2 subtype strain) | 0.008 | 0.39 |
| (B strain) | 0.004 | 0.54 |
| | 0.008 | 0 |

7. Cytokine Quantification

Based on "18. Cytokine quantification 1" of Example 2, cytokine was quantified. Table 40 shows the results of quantification of cytokines (IL-1β and IFN-α) of the virus-like particles A/NY strain, and Table 41 shows the results of quantification of cytokines of the B/BR strain. It was understood that, in a case where the virus-like particles are used, the amount of inflammatory cytokines becomes smaller than in a case where the whole particle antigens (formalin fixation) are used. This result showed that side reactions are more easily suppressed in the virus-like particles than in the whole particle antigens.

TABLE 40

A/NY strain (H3N2 subtype strain): Results of cytokine quantification (pg/mL)

| | GA concentration (w/v %) | IL-1β | IFN-α |
|---|---|---|---|
| Virus-like particles | 0.004 | 13.1 | 2.7 |
| | 0.008 | 16.3 | 7.0 |
| Whole particle antigens | | 41.3 | 404.7 |

TABLE 41

| B/BR strain (B strain): Results of cytokine quantification (pg/mL) | | | |
|---|---|---|---|
| | GA concentration (w/v %) | IL-1β | IFN-α |
| Virus-like particles | 0.004 | 16.4 | 26.8 |
| | 0.008 | 17.7 | 33.4 |
| Whole particle antigens | | 27.7 | 224.9 |

Example 5

Preparation of Influenza Virus-Like Particles 1. 1-Ethyl-3-[3-Dimethylaminopropyl]Carbodiimide Hydrochloride (EDC) Treatment (Step of Fixing by Reacting Amino Group with Carboxyl Group of a Virus Particle so as to Generate Amide Bond)

EDC was diluted with PBS such that a concentration thereof became 4 to 0.1 M. The influenza A viruses (H3N2 subtype strain (A/NY strain)) and the influenza B viruses (B/BR strain) were purified in the same manner as in Example 1. After being purified, the influenza virus particles were inactivated using BPL, added to the EDC solution which was diluted such that the EDC concentration became 0.5 to 0.005 M, and reacted for 2 hours at 4° C. At this time, a protein concentration in the reaction solution was set to be 2,500 μg/mL. After the reaction ended, the reaction solution was dialyzed using PBS such that EDC was removed, thereby obtaining a suspension B1 (A/NY strain) and a suspension B2 (B/BR strain) containing the fixed influenza virus particles.

2. Ether Treatment (Step of Performing Delipidation Treatment on Fixed Influenza Virus Particles)

Polysorbate 80 was added to the suspension B1 and the suspension B2 containing the influenza virus particles treated with EDC such that a final concentration thereof became 0.05 vol %. Then, diethyl ether (delipidation agent) was added to the suspension B1 or the suspension B2 such that a final concentration thereof became 33 vol %, followed by stirring for 1 hour at 25° C. The obtained mixed solution was then subjected to centrifugation at 3,000 rpm for 5 minutes at 4° C., and a water phase was recovered, thereby removing an ether phase. Through the aforementioned step, influenza virus-like particles as a sample were prepared.

The lipid-component content of the obtained influenza virus-like particles was measured using an Amplex Red Cholesterol Assay Kit (manufactured by Invitrogen, trade name). The sample containing the influenza virus-like particles was subjected to ultracentrifugation (24,000 rpm, 2 hrs, 4° C.) such that the sample was separated into supernatant and a pellet component. The obtained pellet component was resuspended in PBS. A fluorescent substance resorufin was added to the resuspended pellet component such that a reaction occurred. By measuring fluorescence intensity of the fluorescent substance resorufin having undergone the reaction, the lipid-component content of the influenza virus-like particles was quantified. As a result, it was confirmed that the lipid-component content of the influenza virus-like particles is at most equal to or less than 50% by mass with respect to the lipid-component content of the influenza virus particles (Table 42).

TABLE 42

| Ratio of cholesterol content of virus-like particles with respect to whole particle antigens (%) | | |
|---|---|---|
| Strain name of virus particles as origin | EDC concentration (M) | Ratio of cholesterol content of virus-like particles |
| A/NY strain | 0.005 | 32 |
| (H3N2 subtype | 0.05 | 30 |
| strain) | 0.5 | 43 |
| B/BR strain | 0.005 | 10 |
| (B strain) | 0.05 | 10 |
| | 0.5 | 15 |

Example 6

Evaluation of Physical Properties

The physical properties of the virus-like particles (sample) obtained in Example 5 were evaluated by the following methods.

1. Analysis by Sucrose Density Gradient Centrifugation Method.

The virus-like particles derived from the H3N2 subtype strain (A/NY strain) were analyzed by a sucrose density gradient centrifugation method. As a typical example, the samples (whole particle antigens and virus-like particles) treated with EDC at an EDC concentration of 0.05 M were placed in a density gradient consisting of layers of 15% to 60% sucrose and subjected to centrifugation at 18,000 rpm for 16 hours at 4° C. After the centrifugation, each fraction was fractionated in an amount of 0.6 mL, and a sucrose concentration, an HA titer, and a protein concentration of each fraction were measured. The results are shown in Table 43. In the virus-like particles, the sample was fractionated to form a single peak at a high sucrose concentration (about 50%), and this showed that the virus-like particles have the same shape (granularity) as inactivated whole particles. The HA activity increased 1,280-fold.

TABLE 43

| A/NY strain (H3N2 subtype strain): sucrose density gradient centrifugation analysis and HA activity in virus-like particles and whole particle antigens | | |
|---|---|---|
| Virus-like particles or whole particle antigens | Virus-like particles | Whole particle antigens |
| Sucrose concentration (%) | 50.2 Single peak | 47.2 Single peak |
| Protein content (μg/mL) | 310.0 | 494.0 |
| HA activity (x) | 1280 | 10240 |

2. Analysis Using Electron Microscope

In order to more specifically investigate the shape of the virus-like particles (derived from the A/NY strain), the virus-like particles were observed with an electron microscope. The aforementioned sample at a concentration of about 500 μg/mL was subjected to fixation for 20 minutes at room temperature by using glutaraldehyde. Then, the fixed sample was loaded on an ion-coated sheet mesh (manufactured by Nisshin EM Co., Ltd.) for observation, leaved to stand for 60 seconds, and subjected to negative staining by using a 2% aqueous phosphotungstic acid solution. The stained sample was observed and imaged using a transmission electron microscope (TECNAI G2 manufactured by FEI.: acceleration voltage 120 kV)

As a typical example, a result is shown which was obtained by observing the virus-like particles that were reacted for 2 hours at 4° C. and an EDC concentration 0.5

Figure 6:
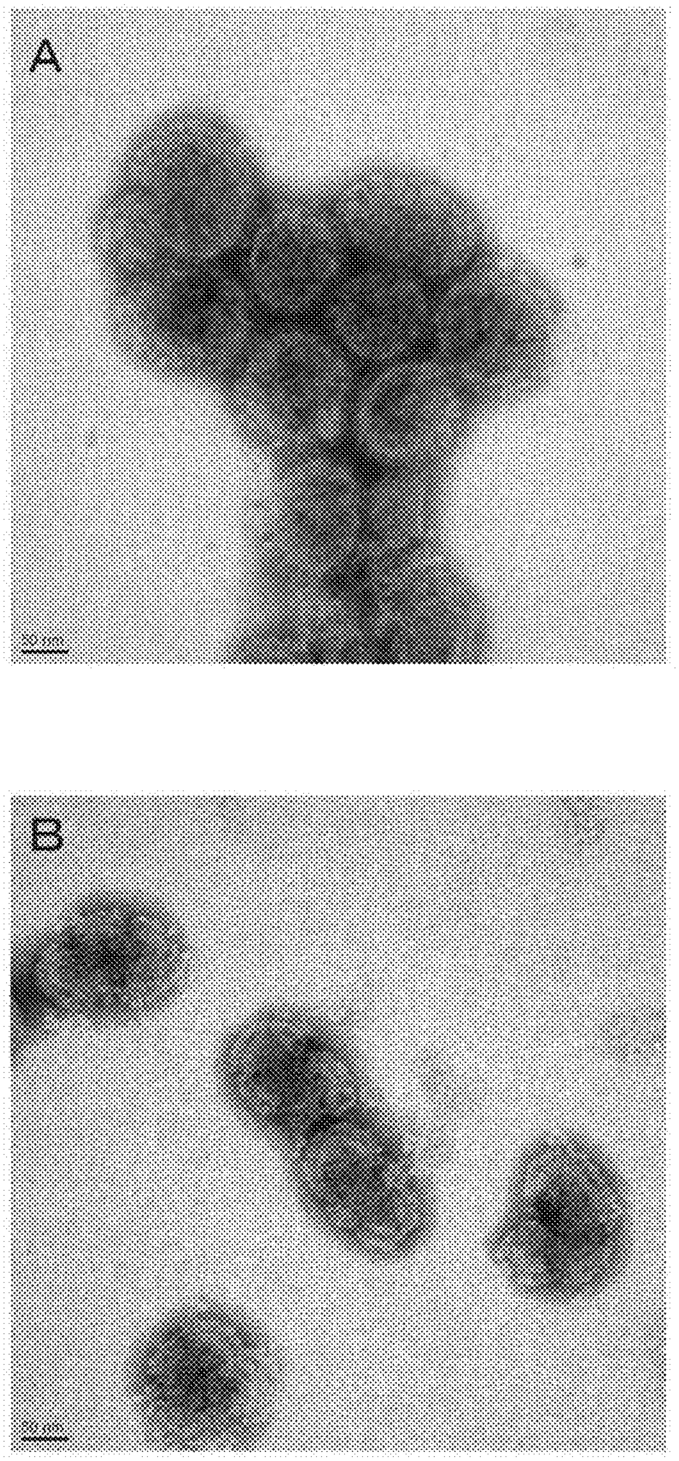
FIG. 6 shows pictures of influenza virus particles and virus-like particles derived therefrom that were taken with an electron microscope (EDC treatment).

M and then treated with ether (FIG. 6(B)). As a control, a result is shown which was obtained by observing whole particle antigens that were reacted for 2 hours at 4° C. and an EDC concentration of 0.5 M (FIG. 6(A)). The virus-like particles maintained the particle structures just like the whole particle antigens. In the observation image in which the envelopes were broken by the ether treatment, and the staining solution permeated the virus-like particles, an aggregate formed by the bonding between the virus-like particles was not observed.

3. Analysis of Genomic Nucleic Acid Derived from Virus Particles (Quantitative Analysis)

The genomic nucleic acid derived from virus particles (referred to as a "virus-derived genomic nucleic acid" in some cases) in virus-like particles was quantitatively investigated. The virus-like particles or the whole particle antigens were diluted with PBS, and SDS and a Proteinase K were added thereto, followed by a reaction for 6 hours at 55° C. Then, by using a TRIzol LS Reagent, a PureLink RNA Mini Kit, and a PureLink DNase (manufactured by Invitrogen, trade names), RNA was extracted. The content of the extracted RNA was measured using Quant-iT RiboGreen RNA Reagent and Kit (manufactured by Invitrogen, trade name).

Table 44 shows a ratio of an RNA content of the virus-like particles with respect to the whole particle antigens. The ratio of RNA remaining in the virus-like particles was about 90% with respect to the whole particle antigens. This results showed that RNA practically remains in the virus-like particles as in the case of formalin treatment, even in a case of EDC treatment.

TABLE 44

Ratio of RNA content of virus-like particles with respect to whole particle antigens (%)

| Strain name of virus particles as origin | EDC concentration (M) | Ratio of RNA content of virus-like particles |
|---|---|---|
| A/NY strain | 0.005 | 92 |
| (H3N2 subtype | 0.05 | 93 |
| strain) | 0.5 | 96 |

4. Immunogenicity 1

The immunogenicity of the virus-like particles was evaluated using mice. ddY mice (females, 8-week-old) were inoculated with the split antigens (formalin inactivation) or the virus-like particles by intramuscular administration at an inoculum amount of 0.8 μg in terms of a protein amount (16 mice per group). Three weeks after immunization, the mice were euthanized and subjected to collection of whole blood. A serum was obtained through centrifugation, and a neutralizing antibody titer was measured. As a typical example, the results of the immunogenicity (neutralizing antibody titer (GMT)) of the virus-like particles, which were reacted for 2 hours at 4° C. in 0.05 M EDC and then treated with ether, are shown in Table 45. In a case of the H3N2 subtype strain, the immunogenicity of the virus-like particles was higher than that of the split antigens. In a case of the B strain, the immunogenicity of the virus-like particles was significantly higher ($P<0.05$) than that of the split antigens.

TABLE 45

Results of immunogenicity (neutralizing antibody titer (GMT))

| Strain name of virus particles as origin | Split antigens | Virus-like particles |
|---|---|---|
| A/NY strain (H3N2 subtype strain) | 682 | 824 |
| B/BR strain (B strain) | 27 | 67 |

5. Fever Test

The virus-like particles were diluted with PBS such that a protein content in 1 mL of the particles became 240 μg, thereby obtaining a sample. Rabbits were inoculated with the sample at a dose of 1 mL/1 kg (body weight), and an increase of rectal temperature caused by fever was observed. Table 46 shows the total increase of rectal temperature (° C.) in three rabbit caused by a febrile reaction.

In none of the virus-like particles treated with ether, a total of equal to or higher than 1.3° C. of the increase of rectal temperature caused by fever was not confirmed.

TABLE 46

Total increase of rectal temperature in three rabbits inoculated with virus-like particles caused by febrile reaction (° C.)

| Strain name of virus particles as origin | EDC concentration (M) | Total increase of rectal temperature caused by febrile reaction (° C.) |
|---|---|---|
| A/NY strain | 0.005 | 0.64 |
| (H3N2 subtype | 0.05 | 0.27 |
| strain) | 0.5 | 0.41 |
| B/BR strain | 0.05 | 0.77 |
| (B strain) | 0.5 | 0.96 |

6. Cytokine Quantification

Based on "18. Cytokine quantification 1" of Example 2, cytokine was quantified. Table 47 shows the results of quantification of cytokines (IL-1β and IFN-α) of the virus-like particle A/NY strain, and Table 48 shows the results of quantification of cytokines of the B/BR strain. It was understood that, in a case where the virus-like particles are used, the amount of inflammatory cytokines becomes smaller than in a case where the whole particle antigens (formalin fixation) are used. This result showed that side reactions are more easily suppressed in the virus-like particles than in the whole particle antigens.

TABLE 47

A/NY strain (H3N2 subtype strain): Results of cytokine quantification (pg/mL)

| | EDC concentration (M) | IL-1β | IFN-α |
|---|---|---|---|
| Virus-like particles | 0.005 | 19.6 | 7.0 |
| | 0.05 | 19.2 | 8.3 |
| Whole particle antigens | | 41.3 | 404.7 |

TABLE 48

| B/BR strain (B strain): Results of cytokine quantification (pg/mL) | | | |
|---|---|---|---|
| | EDC concentration (M) | IL-1β | IFN-α |
| Virus-like particles | 0.005 | 14.3 | 14.9 |
| | 0.05 | 10.9 | 28.7 |
| Whole particle antigens | | 27.7 | 224.9 |

Example 7

Preparation of Japanese Encephalitis Virus-Like Particles

1. Glutaraldehyde Treatment (Step of Fixing Particle Structures of Virus Particles)

Glutaraldehyde was added to a Vero cell-cultured Japanese encephalitis original vaccine (manufactured by The Chemo-Sero-Therapeutic Research Institute, trade name "ENCEVAC" (inactivated using 0.08% formalin), suspension A) such that a final concentration thereof became 0.002 to 0.05 vol %, followed by a reaction for 3 days at 4° C. After the reaction ended, the obtained reaction solution was dialyzed using PBS to which lactose (final concentration: 5 w/v %) was added as an activator. The glutaraldehyde was removed through the dialysis, thereby obtaining a suspension B containing fixed Japanese encephalitis virus particles.

2. Ether Treatment (Step of Performing Delipidation Treatment on Fixed Virus Particles)

Diethyl ether of the same volume and polysorbate 80 were added to the suspension B such that the final concentration of polysorbate 80 became 0.01 vol %, followed by stirring for 1 hour at room temperature. The obtained solution was subjected to centrifugation at 3,000 rpm for 5 minutes at 4° C., a water phase was then recovered, and an ether phase was removed. Through the aforementioned step, Japanese encephalitis virus-like particles as a sample were prepared.

Example 8

Evaluation of Physical Properties

The physical properties of the virus-like particles (sample) obtained in Example 7 were evaluated by the following methods.

1. Analysis Using Electron Microscope

In order to specifically investigate the shape of the virus-like particles, the virus-like particles were observed with an electron microscope. The aforementioned sample at a concentration of about 70 μg/mL was loaded on an ion-coated sheet mesh (manufactured by Nisshin EM Co., Ltd.) for observation, allowed to stand for about 60 seconds, and subjected to negative staining by using a 2% aqueous phosphotungstic acid solution. The stained sample was observed and imaged using a transmission electron microscope (TECNAI G2 manufactured by FEI.: acceleration voltage 120 kV)

Figure 7:
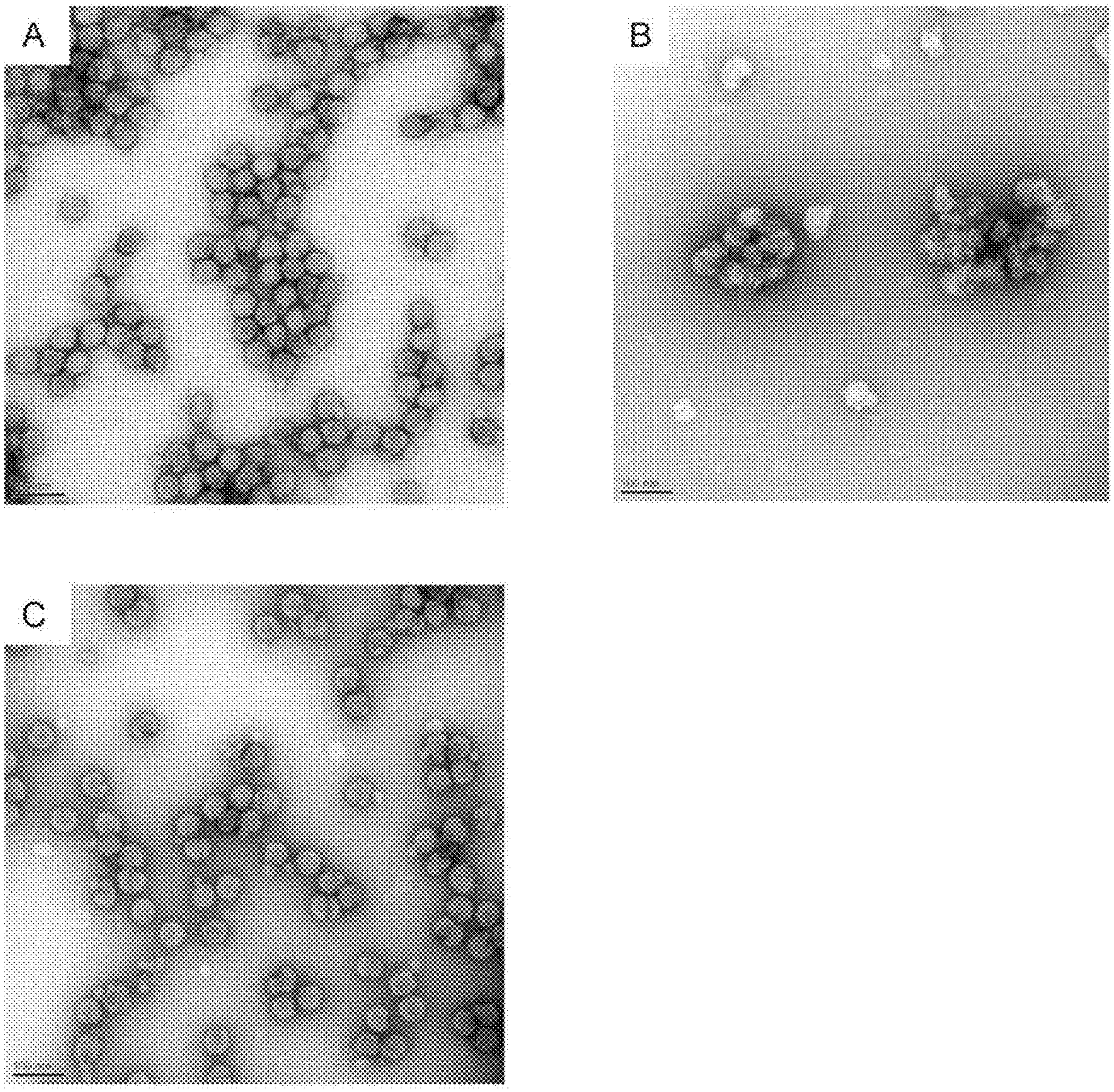
FIG. 7 shows pictures of Japanese encephalitis virus particles and virus-like particles derived therefrom that were taken with an electron microscope (glutaraldehyde treatment).

As a typical example, a result is shown which was obtained by observing the virus-like particles that were reacted for 3 days at 4° C. and a glutaraldehyde concentration of 0.01 w/v % and then treated with ether (FIG. 7(C)). As a control, a result is shown which was obtained by observing the virus-like particles that were treated with ether without being subjected to glutaraldehyde fixation (FIG. 7(B)), and a result is shown which was obtained by observing the Vero cell-cultured Japanese encephalitis original vaccine (FIG. 7(A)). Due to the glutaraldehyde fixation, the virus-like particles maintained the particle structures just like the Vero cell-cultured Japanese encephalitis original vaccine. In contrast, the virus-like particles not being subjected to glutaraldehyde fixation were found to form an aggregate.

2. Dynamic Light Scattering

The mean particle size of the virus-like particles was analyzed using Particle Sizing System: NICOMP 380 ZLS-S. Table 49 shows the mean particle size in a liquid determined by a dynamic light scattering method. The virus-like particles had a mean particle size of about 90 nm substantially appeared as a single peak. In contrast, the Vero cell-cultured Japanese encephalitis original vaccine had a mean particle size of about 80 nm substantially appeared as a single peak. From these results, it was understood that the mean particle size obtained after the ether treatment is slightly greater than that of the virus particles not being treated with ether, and the mean particle size substantially does not change even after delipidation performed by ether treatment. From the dynamic light scattering experiment, it was confirmed that the virus-like particles maintain the particle structures, and an impurity such as an aggregate was not observed.

TABLE 49

| Mean particle size in liquid determined by dynamic light scattering method (volume-weighted mean particle size (main peak (%) (nm))) | | |
|---|---|---|
| | Virus-like particles | Vero cell-cultured Japanese encephalitis original vaccine |
| Volume-weighted mean particle size (main peak) (nm) | 95.1 (96.78%) | 79.8 (95.77%) |

3. Content of Antigen

The content of antigens (antigen content) was measured by a sandwich ELISA method using an anti-Japanese encephalitis virus antibody. An E antigen contained in the sample is trapped in a microplate to which anti-Japanese encephalitis virus rabbit IgG (primary antibody; polyclonal antibody) is bonded. Then, by reacting the antigen with an anti-Japanese encephalitis virus B protein monoclonal antibody (secondary antibody; monoclonal antibody) to which horseradish-derived peroxidase (HRP) is boned, a complex of anti-E antigen antibody/E antigen/secondary antibody bonded to the plate is formed. The reagent and the sample remaining unreacted are washed off. When the complex is reacted with an enzyme substrate solution (o-phenylenediamine solution:OPD solution), HRP on the E antigen complex reacts, and hence a chromogenic reaction occurs. By exploiting the fact that the intensity of the chromogenic reaction of OPD is proportional to the amount of the complex (reflecting the amount of the E antigen), the amount of the E antigen was measured.

As a typical example, Table 50 shows the amount of antigens in the virus-like particles (virus-like particles to which 0.005% polysorbate 80 was added and which were then treated with ether and virus-like particles treated with ether without the addition of polysorbate 80), which were reacted for 3 days at 4° C. and a glutaraldehyde concentration of 0.01 w/v % and then treated with ether), the amount of antigens in the virus-like particles treated with ether without being subjected to glutaraldehyde fixation, and the amount of antigens in the Vero cell-cultured Japanese encephalitis original vaccine. In the sample to which the polysorbate 80 was not added and the sample not being subjected to glutaraldehyde fixation, the amount of antigens was less than 6.25 μg/mL. In contrast, the amount of antigens in the virus-like particles, to which 0.005% polysorbate 80 was added, was the same as the amount of antigens in the Vero cell-cultured Japanese encephalitis original vaccine.

TABLE 50

| Results of antigen content (μg/mL) | | | | |
|---|---|---|---|---|
| | Virus-like particles (addition of polysorbate 80) | Virus-like particles (without addition of polysorbate 80) | Virus-like particles (without glutaraldehyde fixation) | Vero cell-cultured Japanese encephalitis original vaccine |
| Antigen content (μg/mL) | 74.0 | Less than 6.25 | Less than 6.25 | 80.0 |

It was revealed that the lipid constituting the membrane of the Japanese encephalitis virus is mostly composed of cholesterol. Therefore, the lipid-component content of the virus-like particles was quantified by measuring the amount of cholesterol as a typical lipid component. The lipid-component content of the obtained Japanese encephalitis virus-like particles was measured using an Amplex Red Cholesterol Assay Kit (manufactured by Invitrogen, trade name). The sample containing the Japanese encephalitis virus-like particles was subjected to ultracentrifugation (28,000 rpm, 6 hrs, 4° C.) such that the sample was separated into supernatant and a pellet component. The obtained pellet component was resuspended in PBS. A fluorescent substance resorufin was added to the resuspended pellet component such that a reactin occurred. By measuring fluorescence intensity of the fluorescent substance resorufin having undergone the reaction, the lipid-component content of the Japanese encephalitis virus-like particles was quantified. As a result, the lipid-component content of the Japanese encephalitis virus-like particles was found to be at most equal to or less than 20% by mass with respect to the lipid-component content of Japanese encephalitis virus particles (Table 51).

TABLE 51

| Ratio of cholesterol content of virus-like particles with respect to whole particle antigens (%) | |
|---|---|
| Ether:suspension B (volume ratio) | Ratio of cholesterol content of virus-like particles |
| 1:1 | 24 |
| 1:2 | Less than 5.2 |
| 1:4 | Less than 5.2 |

4. Analysis of Genomic Nucleic Acid Derived from Virus Particles (Quantitative Analysis)

The genomic nucleic acid derived from virus particles (referred to as a "virus-derived genomic nucleic acid" in some cases) in the virus-like particles was quantitatively investigated. The virus-like particles or the whole particle antigens were diluted with PBS, and SDS and a Proteinase K were added thereto, followed by a reaction for 54 hours at 55° C. Then, by using a TRIzol LS Reagent, a PureLink RNA Mini Kit, and a PureLink DNase (manufactured by Invitrogen, trade names), RNA was extracted. The content of the extracted RNA was measured using Quant-iT RiboGreen RNA Reagent and Kit (manufactured by Invitrogen, trade name).

Table 52 shows a ratio of an RNA content of the virus-like particles with respect to the whole particle antigens. It was found that the ratio of RNA remaining in the virus-like particles is about 70% with respect to the whole particle antigens (Table 52).

TABLE 52

| Ratio of RNA content of virus-like particles with respect to whole particle antigens (%) | |
|---|---|
| Ether:suspension B (volume ratio) | Ratio of RNA content of virus-like particles |
| 1:1 | 84 |
| 1:2 | 74 |
| 1:4 | 74 |

5. Cytokine Quantification

As a method alternative to the fever test, the amount of cytokine was evaluated using an inflammatory cytokine measurement system using human PBMC. The amount of cytokine was measured for IL-1β and IL-6 which are typical inflammatory cytokines. The human peripheral blood mononuclear cells (PBMC) were suspended in FCS containing MEM medium and diluted at $4\times10^6$ cells/mL. The cells were added in an amount of 100 μL to a 96-well plate, and the virus-like particles or the Vero cell-cultured Japanese encephalitis original vaccine were added thereto in the same amount (final concentration: 25 μg/mL). Then, the cells were cultured for 24 hours at 37° C. in a $CO_2$ atmosphere, and IL-1β and IL-6 in the supernatant were quantified by an ELISA method. As a typical example, the results of quantification of the cytokines (IL-1β and IL-6) of the sample, which was reacted for 3 days at 4° C. and a glutaraldehyde concentration of 0.01 w/v % and then treated with ether, are shown in Table 53. The content of both of IL-1β and IL-6 was smaller in the virus-like particles than in the Vero cell-cultured Japanese encephalitis original vaccine. This result showed that side reactions are more easily suppressed in the virus-like particles than in the Vero cell-cultured Japanese encephalitis original vaccine.

TABLE 53

| Result of cytokine quantification (pg/mL) | | |
|---|---|---|
| | Virus-like particles (addition of polysorbate 80) | Vero cell-cultured Japanese encephalitis original vaccine |
| IL-1β | 3.3 | 324.2 |
| IL-6 | 5.7 | 210.7 |

6. Immunogenicity (Mouse)

ddY mice (females, 4-week-old) were inoculated with, as a typical example, the virus-like particles (virus-like particles to which 0.005% polysorbate 80 was added and which were then treated with ether), which were reacted for 3 days at 4° C. and a glutaraldehyde concentration of 0.01 w/v % and then treated with ether, or with the Vero cell-cultured Japanese encephalitis original vaccine by intraperitoneal administration at an inoculum amount of 4 μg or 1 μg (10 mice per group). One week after immunization, the mice were immunized again, and 1 week thereafter, the mice were euthanized and subjected to collection of whole blood. A serum was obtained through centrifugation and pooled in an equal amount for each group, and a neutralizing antibody titer was measured. Table 54 shows the results calculated from a 50% reduction rate of the number of plaques. The neutralizing antibody titer of the virus-like particles treated with ether was equal to or higher than that of the Vero cell-cultured Japanese encephalitis original vaccine.

TABLE 54

Results of immunogenicity (neutralizing antibody titer)

| Inoculum amount (μg) | Virus-like particles | Vero cell-cultured Japanese encephalitis original vaccine |
|---|---|---|
| 4 | $10^{4.1}$ | $10^{3.3}$ |
| 1 | $10^{3.4}$ | $10^{3.0}$ |

7 Immunogenicity (Crab-Eating Macaque)

Crab-eating macaques (females, about 8-year-old) were inoculated with, as a typical example, the virus-like particles (virus-like particles to which 0.01% polysorbate 80 were added and which were then treated with ether), which were reacted for 3 days at 4° C. and a glutaraldehyde concentration of 0.01 w/v % and then treated with ether, or with the Vero cell-cultured Japanese encephalitis original vaccine by intraperitoneal administration at an inoculum amount of 4 μg (3 monkeys per group). Three weeks after immunization, the monkeys were immunized again, and 4 weeks thereafter, partial blood collection was performed. A serum was obtained through centrifugation and pooled in an equal amount for each group, and a neutralizing antibody titer was measured. Table 55 shows the results calculated from a 50% reduction rate of the number of plaques. The virus-like particles treated with ether induced a sufficient amount of neutralizing antibodies just like the Vero cell-cultured Japanese encephalitis original vaccine.

TABLE 55

Results of immunogenicity (neutralizing antibody titer) (crab-eating macaque)

| Number of time of immunization | Virus-like particles | Vero cell-cultured Japanese encephalitis original vaccine |
|---|---|---|
| After primary immunization | $10^{4.0}$ | $10^{4.0}$< |
| After secondary immunization | $10^{3.7}$ | $10^{4.0}$< |

Example 9

Preparation of HBs Virus-Like Particles

1. Formaldehyde Treatment (Step of Fixing Particle Structures for Virus Particles)

An HBs antigen solution (suspension A) was stirred, and at the same time, formaldehyde was added thereto such that a final concentration thereof became 0.018 to 0.162 w/v %, thereby causing a reaction. After the reaction ended, the reaction solution was dialyzed using PBS such that formaldehyde was removed, thereby obtaining a suspension B containing fixed HBs particles.

2. Ether Treatment (Step of Performing Delipidation Treatment on Fixed Virus Particles)

Polysorbate 80 was added to the suspension B such that a final concentration thereof became 0.05 vol %. Then, diethyl ether (delipidation agent) having the same volume as the suspension B was added thereto such that a final concentration thereof became 50 vol %, followed by stirring for 1 hour at 25° C. The obtained mixed solution was then subjected to centrifugation at 3,000 rpm for 5 minutes at 4° C., and a water phase (suspension C) was recovered, thereby removing an ether phase.

3. Addition of Aluminum Salt

The suspension C was mixed with an aluminum salt. Through the aforementioned step, HBs virus-like particles as a sample were prepared.

Example 10

Evaluation of Physical Properties

The physical properties of the virus-like particles (sample) obtained in Example 9 were evaluated by the following methods.

1. Analysis Using Electron Microscope

In order to specifically investigate the shape of the virus-like particles, the virus-like particles were observed with an electron microscope. The sample having a concentration of about 25 μg/mL was loaded on an ion-coated sheet mesh (manufactured by Nisshin EM Co., Ltd.) for observation, allowed to stand for about 60 seconds, and subjected to negative staining by using a 2% aqueous phosphotungstic acid solution. The stained sample was observed and imaged using a transmission electron microscope (TECNAI G2 manufactured by FEI.: acceleration voltage 120 kV)

Figure 8:
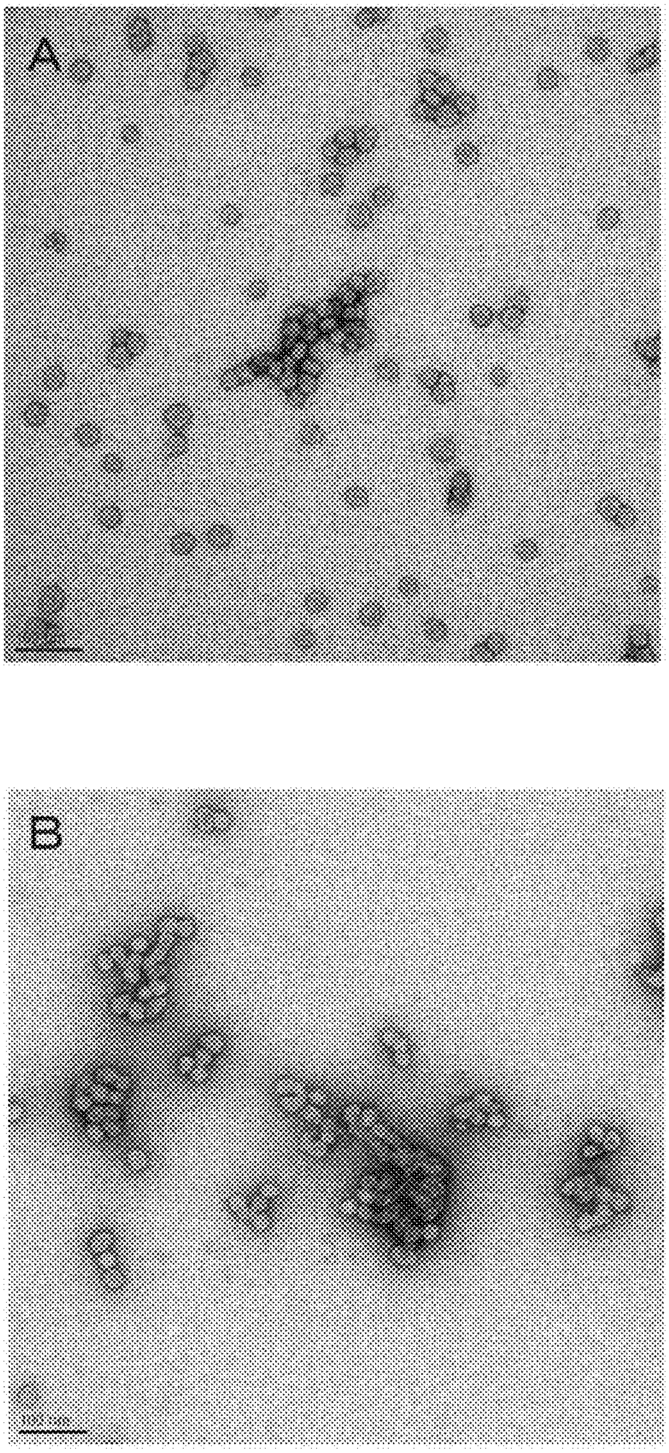
FIG. 8 shows pictures of precipitated recombinant hepatitis B virus-like particles and virus-like particles derived therefrom that were taken with an electron microscope (formalin treatment).

As a typical example, a result is shown which was obtained by observing the virus-like particles that were reacted for 96 hours at 37° C. and a formaldehyde concentration of 0.05 w/v % and then treated with ether (FIG. 8(B)). As a control, a result is shown which was obtained by observing whole particles that were subjected only to formalin fixation without being treated with ether (FIG. 8(A)). Due to the formalin fixation, the virus-like particles maintained the particle structures just like the HBs whole particles.

2. Content of Antigen

By a one-step sandwich EIA method using a high affinity anti-HBs mouse monoclonal antibody, the content of antigens (antigen content) was measured. The antigen content was measured using a fully automated enzyme immunoassay device AIA (manufactured by Tosoh Corporation, trade name). Into a reagent cup used for the measurement, antibodies fixed to magnetic beads and alkaline phosphatase-labeled antibodies are sealed as freeze-dried antibodies. By adding a sample to the reagent cup, an antigen-antibody reaction was caused for a certain period of time at a certain temperature. After the reaction, the magnetic beads were washed with cleaning water, thereby removing the liberated enzyme-labeled antibodies and sample components. Then, in order to measure the enzyme activity of the alkaline phosphotase-labeled antibodies bonded to the magnetic beads, 4-methylumbelliferyl phosphate was added thereto as an enzyme substrate. By measuring a generation rate of a fluorescent substance (4-methylumbelliferone) obtained as a result of the enzyme reaction, the concentration of HBs antigens in the sample was measured.

As a typical example, the virus-like particles, which were reacted for 96 hours at 37° C. and a formaldehyde concentration of 0.05 w/v % and then treated with ether, were used. As a control, a precipitated recombinant hepatitis B vaccine (manufactured by The Chemo-Sero-Therapeutic Research Institute, trade name "BIMMUGEN") was used. Table 56 shows the values of specific activity obtained by dividing the antigen content (ng/mL) of each sample by a protein concentration (ng/mL). The virus-like particles to which 0.005% polysorbate 80 was added contained antigens in the same amount as the precipitated recombinant hepatitis B vaccine.

TABLE 56

Results of specific activity obtained by dividing antigen content by protein concentration

| | Virus-like particles (addition of polysorbate 80) | Virus-like particles (without addition of polysorbate 80) | Precipitated recombinant hepatitis B vaccine |
|---|---|---|---|
| Specific activity | 0.112 | 0.058 | 0.142 |

3. Dynamic Light Scattering

The mean particle size of the virus-like particles was analyzed using Zetasizer Nano ZS (manufactured by Malvern Instruments Ltd). As a typical example, the result obtained from the virus-like particles, which were reacted for 96 hours at 37° C. and a formaldehyde concentration of 0.05 w/v % and then treated with ether, is shown in Table 57. Furthermore, as a control, the result obtained from the precipitated recombinant hepatitis B vaccine is shown in Table 57. Both of the virus-like particles and the vaccine had a mean particle size of around 100 nm appeared as a single peak. This result showed that the mean particle size of the virus-like particles treated with ether is the same as the particle size of the virus particles, the virus-like particles have a single mean particle size, and the mean particle size does not change. From the dynamic light scattering experiment, it was confirmed that the virus-like particles maintain the particle structures, and an impurity such as an aggregate was not observed.

TABLE 57

Mean particle size in liquid determined by dynamic light scattering

| | Virus-like particles (addition of polysorbate 80) | Precipitated recombinant hepatitis B vaccine |
|---|---|---|
| Volume-weighted mean particle size (nm) | 104<br>Single peak | 90<br>Single peak |

4. Test for Content of Phosphatidylcholine

Phosphatidylcholine accounts for 80% or more of lipid components contained in the HBs antigen. Therefore, the lipid-component content of the HBs antigens was quantified by measuring the content of phosphatidylcholine as a typical lipid component. The content of phosphatidylcholine was measured using a Phosphatidylcholine Assay Kit (manufactured by Cell Biolabs, Inc, trade name). In the presence of catalyst horseradish-derived peroxidase (HRP), hydrogen peroxide generated in the process of reaction was detected using a high-sensitive fluorescence probe, and the fluorescence intensity was measured, thereby measuring the content of phosphatidylcholine. As a typical example, the result obtained from the virus-like particles, which were reacted for 96 hours at 37° C. and a formaldehyde concentration of 0.05 w/v % and then treated with ether, is shown in Table 58. As a control, a result obtained from the precipitated recombinant hepatitis B vaccine is shown in Table 58. The content of phosphatidylcholine in the virus-like particles was found to be at most equal to or less than 59% by mass with respect to the control.

TABLE 58

Ratio of phosphatidylcholine content of virus-like particles with respect to precipitated recombinant hepatitis B vaccine

| | Virus-like particles (addition of polysorbate 80) | Precipitated recombinant hepatitis B vaccine |
|---|---|---|
| Phosphatidylcholine content (% by mass) | 59 | 100 |

5. Immunogenicity (Mouse)

BALB/c mice and C57BL/6 mice (females, 5-week-old) were inoculated with the virus-like particles (virus-like particles to which 0.005% polysorbate 80 was added and which were then treated with ether), which were reacted for 96 hours at 37° C. and a formaldehyde concentration of 0.05 w/v % and then treated with ether, or with the precipitated recombinant hepatitis B vaccine by intramuscular administration at an inoculum amount of 2 μg or 0.5 μg (8 mice per group). Four weeks after immunization, the mice were immunized again, and 4 weeks thereafter, the mice were euthanized and subjected to collection of whole blood. A serum was obtained through centrifugation, and an antibody titer in the serum was measured using a fully automated enzyme immunoassay device AIA (manufactured by Tosoh Corporation, trade name). The antibody titer was measured by a one-step sandwich EIA method using a solid layer and HBs antigens as enzyme-labeled antigens. Into a reagent cup used for the measurement, antibodies fixed to magnetic beads and alkaline phosphatase-labeled antibodies are sealed as freeze-dried antibodies. By adding a sample to the reagent cup, an antigen-antibody reaction was caused for a certain period of time at a certain temperature. After the reaction, the magnetic beads were washed with cleaning water, thereby removing the unreacted enzyme-labeled antibodies. Then, in order to measure the enzyme activity of the alkaline phosphotase-labeled antibodies bonded to the magnetic beads, 4-methylumbelliferyl phosphate was added thereto as an enzyme substrate. By measuring a generation rate of a fluorescent substance (4-methylumbelliferone) obtained as a result of the enzyme reaction, the concentration of anti-HBs antibodies in the sample was measured. The results are shown in Table 59. The immunogenicity of the virus-like particles treated with ether was equal to or higher than the immunogenicity of the precipitated recombinant hepatitis B vaccine.

TABLE 59

Result of immunogenicity (antibody titer GMT)

| | BALB/c | | C57BL/6 | |
|---|---|---|---|---|
| Inoculum amount (μg) | Virus-like particles | Precipitated recombinant hepatitis B vaccine | Virus-like particles | Precipitated recombinant hepatitis B vaccine |
| 2 | $10^{4.9}$ | $10^{5.1}$ | $10^{4.3}$ | $10^{4.6}$ |
| 0.5 | $10^{4.6}$ | $10^{4.6}$ | $10^{4.2}$ | $10^{3.8}$ |

INDUSTRIAL APPLICABILITY

The present invention is useful in the field of pharmaceutical products, particularly, in the field of vaccines.

The invention claimed is:

1. A vaccine comprising:

virus-like particles derived from virus particles having an envelope, wherein the particle structures of the virus-like particles are fixed with a fixative and a lipid-component content of the virus-like particles is reduced relative to a lipid-component content of the virus particles.

2. The vaccine according to claim 1, wherein the lipid-component content of the virus-like particles is less than 50% by mass based on the lipid-component content of the virus particles.

3. The vaccine according to claim 1, wherein the lipid-component content of the virus-like particles is less than 20% by mass based on the lipid-component content of the virus particles.

4. The vaccine according to claim 1, wherein the lipid component is cholesterol.

5. The vaccine according to claim 1, wherein the virus-like particles contain a surface antigen of the virus particles, a matrix protein or a membrane protein of the virus particles, and a nucleoprotein of the virus particles.

6. The vaccine according to claim 1, wherein the virus-like particles contain a genomic nucleic acid derived from the virus particles.

7. The vaccine according to claim 1, wherein the virus particles are orthomyxovirus particles, flavivirus particles, or hepatitis B virus particles.

8. The vaccine according to claim 7, wherein the virus particles are influenza virus particles, Japanese encephalitis virus particles, or hepatitis B virus surface antigen (HBs) particles.

9. The vaccine according to claim 8, wherein the virus particles are influenza virus particles.

10. The vaccine according to claim 9, wherein the influenza virus particles are influenza A virus particles or influenza B virus particles.

11. The vaccine according to claim 9, wherein the influenza virus particles are classified into an H1N1 subtype strain, an H2N2 subtype strain, an H3N2 subtype strain, an H3N8 subtype strain, an H5N1 subtype strain, an H5N2 subtype strain, an H5N6 subtype strain, an H6N1 subtype strain, an H7N3 subtype strain, an H7N7 subtype strain, an H7N9 subtype strain, an H9N2 subtype strain, or an H10N8 subtype strain.

12. The vaccine according to claim 8, wherein the surface antigen contains hemagglutinin (HA) or neuraminidase (NA).

13. The vaccine according to claim 1, wherein the matrix protein or the membrane protein contains an M1 protein or an M2 protein.

14. The vaccine according to claim 1, wherein the virus-like particles have a mean particle size that is 70% to 130% of a particle size of the virus particles.

15. The vaccine according to claim 1, wherein the virus-like particles form a peak detected at a sucrose concentration of equal to or higher than 35% when being measured by sucrose density gradient centrifugation.

* * * * *